(12) United States Patent
Hebert et al.

(10) Patent No.: US 12,409,309 B2
(45) Date of Patent: Sep. 9, 2025

(54) CONNECTOR ASSEMBLIES

(71) Applicant: Bard Peripheral Vascular, Inc., Tempe, AZ (US)

(72) Inventors: Casey Tyler Hebert, Tempe, AZ (US); Mark Nicholas Wright, Gilbert, AZ (US); Brandon David Simmons, Tempe, AZ (US); Christopher Dean Drobnik, Wauconda, IL (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 956 days.

(21) Appl. No.: 17/055,757

(22) PCT Filed: May 17, 2019

(86) PCT No.: PCT/US2019/032987
§ 371 (c)(1),
(2) Date: Nov. 16, 2020

(87) PCT Pub. No.: WO2019/222701
PCT Pub. Date: Nov. 21, 2019

(65) Prior Publication Data
US 2021/0236795 A1   Aug. 5, 2021

Related U.S. Application Data

(60) Provisional application No. 62/673,632, filed on May 18, 2018, provisional application No. 62/673,628, filed on May 18, 2018.

(51) Int. Cl.
*A61M 39/00*     (2006.01)
*A61K 51/00*     (2006.01)
(Continued)

(52) U.S. Cl.
CPC ......... *A61M 39/1011* (2013.01); *A61K 51/00* (2013.01); *A61N 5/1007* (2013.01);
(Continued)

(58) Field of Classification Search
CPC .............. A61M 2039/1033; A61M 2039/1038
See application file for complete search history.

(56) References Cited

U.S. PATENT DOCUMENTS

| 4,313,440 | A |   | 2/1982 | Ashley |
| 5,125,915 | A | * | 6/1992 | Berry ................ A61M 39/0613 |
|   |   |   |   | 604/533 |

(Continued)

FOREIGN PATENT DOCUMENTS

| CN | 106232173 A | 12/2016 |
| DE | 3035290 A1  | 4/1982 |

(Continued)

OTHER PUBLICATIONS

Office Action dated Jan. 5, 2023 pertaining to Chinese Office Action 201980042280.3.

(Continued)

*Primary Examiner* — William R Carpenter
(74) *Attorney, Agent, or Firm* — Dinsmore & Shohl, LLP

(57) ABSTRACT

In one aspect, a connector assembly includes a delivery conduit defining a conduit lumen and a securable connector configured to secure the delivery conduit to a medical device hub defining a medical device hub lumen. The conduit lumen includes a constant diameter region along a portion of the delivery conduit and a transition region extending from the delivery conduit to the distal end. A transition region diameter of the transition region gradually increases from the constant diameter region to a distal end of the delivery conduit. The securable connector is coupled to an outer surface of the delivery conduit and is slidable along a portion (Continued)

thereof. The securable connector is configured to receive the medical device hub. The securable connector is secured relative to the delivery conduit so as to fluidically couple the conduit lumen with the medical device hub lumen.

17 Claims, 13 Drawing Sheets

(51) Int. Cl.
 *A61M 39/10* (2006.01)
 *A61N 5/10* (2006.01)
 *A61M 25/00* (2006.01)

(52) U.S. Cl.
 CPC . *A61M 25/0097* (2013.01); *A61M 2039/1072* (2013.01); *A61M 2039/1077* (2013.01); *A61M 2205/0216* (2013.01); *A61N 2005/1021* (2013.01)

(56) References Cited

U.S. PATENT DOCUMENTS

| | | | |
|---|---|---|---|
| 5,478,323 | A | 12/1995 | Westwood et al. |
| 5,496,284 | A | 3/1996 | Waldenburg |
| 5,620,427 | A | 4/1997 | Werschmidt et al. |
| 6,152,913 | A | 11/2000 | Feith et al. |
| 6,508,807 | B1 | 1/2003 | Peters |
| 6,606,370 | B1 | 8/2003 | Kasprowicz |
| 6,629,962 | B2 * | 10/2003 | Correa ............... A01K 45/007 D24/114 |
| 6,723,074 | B1 | 4/2004 | Halseth |
| 7,083,605 | B2 | 8/2006 | Miyahara |
| 7,713,239 | B2 | 5/2010 | Uber, III et al. |
| 2001/0021826 | A1 | 9/2001 | Winkler |
| 2002/0000253 | A1 | 1/2002 | Fillmore et al. |
| 2003/0153897 | A1 | 8/2003 | Russo |
| 2003/0201639 | A1 * | 10/2003 | Korkor ............... F16L 19/0237 285/81 |
| 2003/0208165 | A1 | 11/2003 | Christensen et al. |
| 2004/0111078 | A1 | 6/2004 | Miyahara |
| 2004/0258614 | A1 | 12/2004 | Line et al. |
| 2005/0085685 | A1 | 4/2005 | Barbut |
| 2006/0033334 | A1 * | 2/2006 | Weber ............... F16L 47/04 285/390 |
| 2006/0064159 | A1 * | 3/2006 | Porter ............... A61M 1/3659 623/1.24 |
| 2006/0091329 | A1 | 5/2006 | Eguchi |
| 2006/0293552 | A1 | 12/2006 | Polsinelli et al. |
| 2007/0129591 | A1 | 6/2007 | Yanke et al. |
| 2007/0141339 | A1 | 6/2007 | Song et al. |
| 2008/0058719 | A1 | 3/2008 | Edwards et al. |
| 2008/0103564 | A1 | 5/2008 | Burkinshaw et al. |
| 2008/0200747 | A1 | 8/2008 | Wagner et al. |
| 2008/0287920 | A1 | 11/2008 | Fangrow et al. |
| 2009/0018498 | A1 | 1/2009 | Chiu et al. |
| 2009/0092677 | A1 | 4/2009 | Richard |
| 2009/0232586 | A1 | 9/2009 | Diodati et al. |
| 2010/0063481 | A1 * | 3/2010 | Hoffman ............... A61M 39/10 604/537 |
| 2010/0084585 | A1 | 4/2010 | Prosser |
| 2012/0190976 | A1 | 7/2012 | Kleinstreuer |
| 2012/0201726 | A1 | 8/2012 | Pearcy et al. |
| 2012/0209057 | A1 | 8/2012 | Siess |
| 2013/0165899 | A1 | 6/2013 | Haueter et al. |
| 2013/0317277 | A1 | 11/2013 | Lemer |
| 2013/0331692 | A1 * | 12/2013 | Mouri ............... A61M 39/1055 604/533 |
| 2014/0046295 | A1 | 2/2014 | Uber, III et al. |
| 2014/0163302 | A1 | 6/2014 | Fox et al. |
| 2014/0207178 | A1 | 7/2014 | Chomas et al. |
| 2014/0236093 | A1 | 8/2014 | Eggert et al. |
| 2014/0257233 | A1 | 9/2014 | Cowan |
| 2014/0276651 | A1 * | 9/2014 | Schultz ............... A61M 39/165 53/425 |
| 2015/0273089 | A1 | 10/2015 | Gray |
| 2015/0285282 | A1 | 10/2015 | Weitz et al. |
| 2016/0296740 | A1 | 10/2016 | Adams et al. |
| 2016/0325047 | A1 | 11/2016 | Vedrine et al. |
| 2016/0331853 | A1 | 11/2016 | Taub |
| 2016/0331998 | A1 | 11/2016 | Hoffman et al. |
| 2017/0065732 | A1 | 3/2017 | Srinivas et al. |
| 2017/0120032 | A1 | 5/2017 | Miyazaki et al. |
| 2017/0151357 | A1 | 6/2017 | Cade |
| 2017/0189569 | A1 | 7/2017 | Souresrafil et al. |
| 2017/0238951 | A1 | 8/2017 | Yang et al. |
| 2017/0304151 | A1 | 10/2017 | Van Den Berg et al. |

FOREIGN PATENT DOCUMENTS

| | | | |
|---|---|---|---|
| DE | 4318101 A1 | 12/1994 | |
| EP | 0795342 A2 | 9/1997 | |
| EP | 2179758 A2 | 4/2010 | |
| FR | 2917981 A1 | 1/2009 | |
| JP | H09327519 A | 12/1997 | |
| JP | 2002543894 A * | 12/2002 | ........ A61M 25/0097 |
| JP | 2003210574 A | 7/2003 | |
| JP | 2006017660 A | 1/2006 | |
| NZ | 588125 A | 10/2012 | |
| WO | 2007008511 A2 | 1/2007 | |
| WO | 2009039203 A2 | 3/2009 | |
| WO | 2011014562 A1 | 2/2011 | |
| WO | 2012006555 A1 | 1/2012 | |
| WO | 2012118687 A1 | 9/2012 | |
| WO | 2013153722 A1 | 10/2013 | |
| WO | 2014165058 A1 | 10/2014 | |
| WO | 2015173612 A1 | 11/2015 | |
| WO | 2016049685 A1 | 4/2016 | |
| WO | 2016161346 A1 | 10/2016 | |
| WO | 2017034965 A1 | 3/2017 | |
| WO | 2017053398 A1 | 3/2017 | |
| WO | 2017157974 A1 | 9/2017 | |
| WO | 2019006099 A1 | 1/2019 | |

OTHER PUBLICATIONS

Office Action dated Oct. 19, 2022, pertaining to Chinese Office Action 201980042280.3.
Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.
Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.
Spreafico, C. et al.; The dosimetric importance of the number of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.
International Search Report and Written Opinion dated Aug. 1, 2019 pertaining to International Application No. PCT/US2019/032983.
International Search Report and Written Opinion dated Dec. 13, 2019 pertaining to International Application No. PCT/US2019/032987.
International Search Report and Written Opinion dated Oct. 16, 2019 pertaining to International Application No. PCT/US2019/032955.
International Search Report and Written Opinion dated Jul. 23, 2019 pertaining to International Application No. PCT/US2019/032950.
International Search Report and Written Opinion dated Sep. 24, 2019 pertaining to International Application No. PCT/US2019/033011.
International Search Report and Written Opinion dated Jul. 26, 2019 pertaining to International Application No. PCT/US2019/032965.
International Search Report and Written Opinion dated Jul. 29, 2019 pertaining to International Application No. PCT/US2019/032954.
International Search Report and Written Opinion dated Aug. 7, 2019 pertaining to International Application No. PCT/US2019/032986.

(56) References Cited

OTHER PUBLICATIONS

Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.

Chung, J. et al.; Novel use of the Surefire antireflux device in subtotal splenic embolization; Journal of Vascular Surgery Cases; Dec. 1, 2015; pp. 242-245; vol. 1, No. 4.

Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.

Hospital Clinics et al.; Y-90 MicroSpheres (SIRSpheres) for treatment of hepatocellular carcinoma; Mar. 1, 2017.

Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.

Sirtex Medical Limited: Sirtex Medical Products Pty Ltd SIR-Spheres (Ytttrium-90 Microspheres); Apr. 1, 2005.

Theragenics Corp.; Therasphere IDOC TM; Aug. 4, 2015.

Tong, A. et al; Yttrium-90 hepatic radioembolization: clinical review and current techniques in interventional radiology and personalized dosimetry; British Journal of Radiology; vol. 89, No. 1062; Jun. 1, 2016.

US FDA; Theresphere IDOC—Humanitarian Device Exemption (HDE); Sep. 14, 2015.

Westcott, M. et al.; The development, commercialization, and clinical context of yttrium-90 radiolabeled resin and glass microspheres; Advances in Radiation Oncology; 2016; vol. 1; pp. 351-364.

Sirtex Medical Limited; SMAC-SIR-Spheres Microspheres Activity Calculator; May 6, 2018.

Office Action dated May 25, 2022, pertaining to Chinese Office Action 201980042280.3.

Evidence 1: "SIFIC Hospital Infection Prevention and Control Supplies Guidelines 2014-2015", Hu Bijie et al., p. 233, Shanghai Science and Technology Press, May 2014.

Evidence 2: "Clinical Nursing Teaching in Internal Medicine", Wang Xining et al., p. 113, Tianjin Science and Technology Translation and Publishing Company, Aug. 2010.

Office Action dated Apr. 19, 2023 pertaining to Chinese Application 201980042280.3.

Examination Report dated Nov. 15, 2023 pertaining to NZ 771146 filed May 17, 2019.

JP Office Action dated Apr. 18, 2024 pertaining to JP application No. 2023-107037 filed Jun. 29, 2023.

Examination Report dated May 3, 2024 pertaining to New Zealand Patent Application No. 771146 filed Dec. 15, 2020.

JP Notice of Allowance dated Sep. 3, 2024 pertaining to JP application 2023-107037 filed Jun. 29, 2023.

* cited by examiner

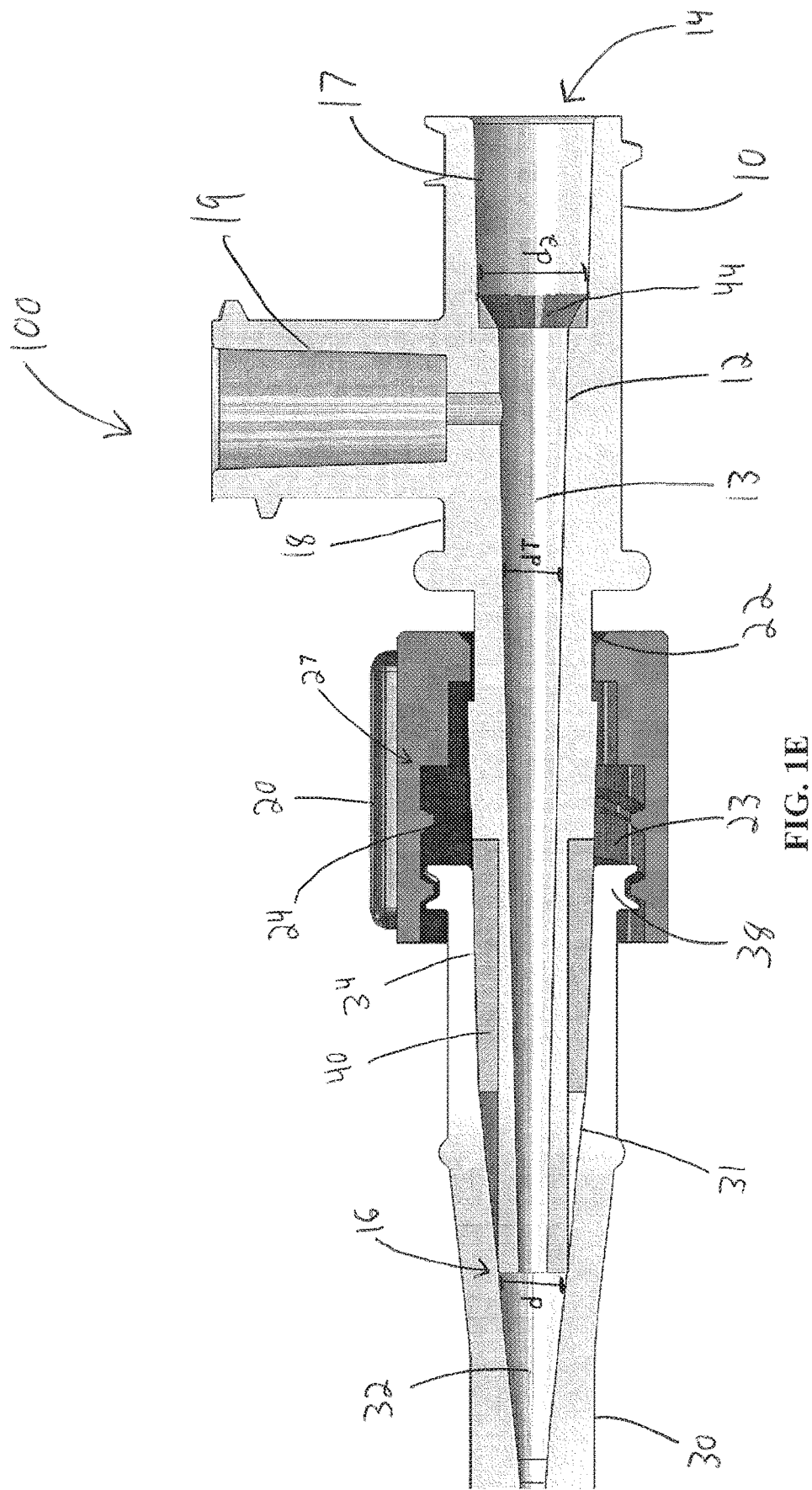

CONNECTOR ASSEMBLIES

CROSS-REFERENCES TO RELATED APPLICATIONS

The present application claims the benefit of U.S. Provisional Pat. App. No. 62/673,628, entitled "DUAL-STAGE SYRINGES WITH LOCKING MECHANISM" filed on May 18, 2018, and U.S. Provisional Pat. App. No. 62/673,632, entitled "RADIOEMBOLIZATION DELIVERY DEVICE" filed on May 18, 2018, the entireties of which are incorporated in this disclosure by reference.

TECHNICAL FIELD

The present disclosure relates generally to connector assemblies, more particularly, to connector assemblies configured to reduce dead space, reduce turbulent flow, create a laminar flow transition, and/or the risk of fluid leakage are desirable.

BACKGROUND

Medical fluids are often delivered to a patient via catheters. These catheters are connected to fluid delivery devices such as syringes or other fluid delivery hubs. Oftentimes, connectors used to connect catheter tubes to fluid delivery devices often have smaller internal diameters than the fluid delivery hub. This may result in dead space within the combined fluid flow path where medical fluid and/or particles can collect. Such collection of fluids, particularly where the fluid is hazardous and/or radioactive is undesirable. For example, a collection of radioactive fluid may increase chances of radiation exposure to operators delivering medical fluid and/or leakage of fluid during disconnect of the catheter from the fluid delivery device.

Accordingly, new connector assemblies that reduce dead space, reduce turbulent flow, create a laminar flow transition, and/or the risk of fluid leakage are desirable.

BRIEF SUMMARY

Connector assemblies as described herein are directed to efficiently delivery fluid and the reduction of dead space within a fluid delivery system in order to prevent undue exposure to a medical fluid delivered through a fluid delivery system.

In a first aspect, a connector assembly includes a delivery conduit defining a conduit lumen extending between a proximal end and a distal end and a securable connector configured to secure the delivery conduit to a medical device hub defining a medical device hub lumen. The conduit lumen comprises a constant diameter region along a portion of the delivery conduit between the proximal end and the distal end and a transition region extending from the delivery conduit to the distal end. A transition region diameter of the transition region gradually increases from the constant diameter region to the distal end of the delivery conduit. The securable connector is coupled to an outer surface of the delivery conduit and is slidable along a portion thereof. The securable connector is configured to receive the medical device hub such that the medical device hub is positioned between the surface of the delivery conduit and the securable connector. The securable connector is secured relative to the delivery conduit so as to fluidically couple the conduit lumen with the medical device hub lumen.

In a second aspect, a connector assembly includes a delivery conduit defining a conduit lumen extending between a proximal end and a distal end, a medical device hub, and a securable connector configured to secure the delivery conduit to the medical device hub defining a medical device hub lumen. The conduit lumen comprises a constant diameter region along a portion of the delivery conduit between the proximal end and the distal end and a transition region extending from the delivery conduit to the distal end. A transition region diameter of the transition region gradually increases from the constant diameter region to the distal end of the delivery conduit. The securable connector is coupled to an outer surface of the delivery conduit and is slidable along a portion thereof. The securable connector is configured to receive the medical device hub such that the medical device hub is positioned between the surface of the delivery conduit and the securable connector. The securable connector is secured relative to the delivery conduit so as to fluidically couple the conduit lumen with the medical device hub lumen.

In a third aspect, the present disclosure includes a connector assembly according to any preceding aspect, further comprising a conformable material disposed between the outer surface of the delivery conduit and an internal surface of the medical device hub.

In a fourth aspect, the present disclosure includes a connector assembly according to the third aspect, wherein the conformable material comprises a thermoplastic elastomer, a thermoplastic vulcanizate, silicone, urethane, polypropylene, or combinations thereof.

In a fifth aspect, the present disclosure includes a connector assembly according to any preceding aspect, wherein the delivery conduit comprises a first port fluidically coupled to the constant diameter region of the conduit lumen; and a second port fluidically coupled to the constant diameter region of the conduit lumen at a non-zero angle relative to the first port.

In a sixth aspect, the present disclosure includes a connector assembly according to any preceding aspect, wherein the delivery conduit comprises a second transition region extending between the proximal end of the conduit and the constant diameter region, wherein the second transition region comprises a transition region diameter that gradually decreases from the proximal end of the delivery conduit to the constant diameter region.

In a seventh aspect, the present disclosure includes a connector assembly according to any preceding aspect, wherein the delivery conduit is formed from a material comprising polycarbonate, polyethylene, polyethylene terephthalate, titanium, aluminum, stainless steel, copper, polyether block amide, or combinations thereof.

In an eighth aspect, the present disclosure includes a connector assembly according to any preceding aspect, wherein the outer surface of the delivery conduit defines a recessed region, and the securable connector is positioned within the recessed region and configured to slide along a length of the recessed region.

In a ninth aspect, the present disclosure includes a connector assembly according to any preceding aspect, wherein the securable connector comprises a luer locking mechanism comprising an internal thread configured to receive an external thread located on an outer surface of the medical device hub.

In a tenth aspect, the present disclosure includes a connector assembly according to any preceding aspect, wherein the transition region diameter of the transition region is approximately equal to the diameter of the medical device hub lumen at a position where the transition region of the delivery conduit engages the medical device hub lumen of the medical device hub.

In an eleventh aspect, the present disclosure includes a connector assembly according to any preceding aspect, wherein the connector assembly is configured to deliver radioembolization fluids, chemoembolization fluids, bland embolization fluids, scout doses, or combinations thereof.

In a twelfth aspect, a connector assembly for connecting two fluid conduits includes a male connector member comprising a male locking mechanism and a stationary septum coupled to the male locking mechanism and a female connector member comprising a female locking mechanism and a fluid delivery conduit disposed within the female locking mechanism, a floating septum coupled to an interior portion of the female locking mechanism, and a biasing mechanism coupling the floating septum to the female locking mechanism and disposed around the fluid delivery conduit. The male locking mechanism is configured to receive a first fluid conduit. The female locking mechanism is configured to receive a second fluid conduit and to engage with the male locking mechanism of the male connector member to fluidically couple the first fluid conduit and the second fluid conduit. The biasing mechanism is configured to bias the floating septum to an extended position, wherein a tip of the fluid delivery conduit contained within a first zone defined by the female locking mechanism and the floating septum. Engagement of the male locking mechanism and the female locking mechanism urges the floating septum into contact with the stationary septum and causes the tip of the fluid delivery conduit to pierce the stationary septum and the floating septum to be positioned within the first fluid conduit. The stationary septum and the floating septum comprise self-healing material configured to create a seal around the fluid delivery conduit as the fluid delivery conduit pierces and extends through the stationary septum and the floating septum as the male connector member becomes engaged with the female connector member.

In a thirteenth aspect, the present disclosure includes a connector assembly for connecting two fluid conduits according to the twelfth aspect, wherein the female connector member of the connector assembly is configured to receive the male connector member of the connector assembly in a twist lock manner.

In a fourteenth aspect, the present disclosure includes a connector assembly for connecting two fluid conduits according to the twelfth aspect or the thirteenth aspect, wherein the male locking mechanism and the female locking mechanism are formed from polycarbonate, polyethylene, polyethylene terephthalate, stainless steel, aluminum, or combinations thereof.

In a fifteenth aspect, the present disclosure includes a connector assembly for connecting two fluid conduits according to any of the twelfth aspect through the fourteenth aspect, wherein the stationary septum of the male connector member and the floating septum of the female connector member are formed from rubber, silicone, or combinations thereof.

In sixteenth aspect, the present disclosure includes a connector assembly for connecting two fluid conduits according to the fifteenth aspect, wherein the stationary septum of the male connector member and the floating septum of the female connector are formed from a material comprising polyisoprene.

In a seventeenth aspect, the present disclosure includes a connector assembly for connecting two fluid conduits according to any of the twelfth aspect through the sixteenth aspect, wherein the fluid delivery conduit of the female connector member comprises a non-coring needle.

In an eighteenth aspect, the present disclosure includes a connector assembly for connecting two fluid conduits according to any of the twelfth aspect through the seventeenth aspect, wherein the male connector member and the female connector member are over-molded with a material comprising thermoplastic elastomer, a thermoplastic vulcanizate, silicone, urethane, polypropylene, or combinations thereof.

In a nineteenth aspect, the present disclosure includes a connector assembly for connecting two fluid conduits according to any of the twelfth aspect through the eighteenth aspect, wherein the biasing mechanism comprises a plastic spring, a metal spring, a rubber spring, or combinations thereof.

In a twentieth aspect, the present disclosure includes a connector assembly for connecting two fluid conduits according to any of the twelfth aspect through the nineteenth aspect, wherein the fluid delivery conduit is stationary relative to the female locking mechanism.

In a twenty-first aspect, a connector assembly includes a delivery conduit defining a conduit lumen extending between a proximal end and a distal end and a securable connector configured to secure the delivery conduit to a medical device hub defining a medical device hub lumen. The securable connector is coupled to an outer surface of the delivery conduit. The securable connector is configured to receive the medical device hub such that the medical device hub is positioned between the surface of the delivery conduit and the securable connector. The securable connector is secured relative to the delivery conduit so as to fluidically couple the conduit lumen with the medical device hub lumen.

In a twenty-second aspect, the present disclosure includes a connector assembly according to the twenty-first aspect, further comprising a conformable material disposed between the outer surface of the delivery conduit and an internal surface of the medical device hub.

In a twenty-third aspect, the present disclosure includes a connector assembly according to the twenty-second aspect, wherein the conformable material comprises a thermoplastic elastomer, a thermoplastic vulcanizate, silicone, urethane, polypropylene, or combinations thereof.

In a twenty-fourth aspect, the present disclosure includes a connector assembly according to any of the twenty-first through twenty-third aspects, wherein the delivery conduit comprises a first port fluidically coupled to the conduit lumen; and a second port fluidically coupled the conduit lumen at a non-zero angle relative to the first port.

In a twenty-fifth aspect, the present disclosure includes a connector assembly according to any of the twenty-first through twenty-fourth aspects, wherein the delivery conduit is formed from a material comprising polycarbonate, polyethylene, polyethylene terephthalate, titanium, aluminum, stainless steel, copper, polyether block amide, or combinations thereof.

In a twenty-sixth aspect, the present disclosure includes a connector assembly according to any of the twenty-first through twenty-fifth aspects, wherein the outer surface of the delivery conduit defines a recessed region, and the securable connector is positioned within the recessed region and configured to slide along a length of the recessed region.

In a twenty-seventh aspect, the present disclosure includes a connector assembly according to any of the twenty-first through twenty-sixth aspects, wherein the securable connector comprises a luer locking mechanism comprising an internal thread configured to receive an external thread located on an outer surface of the medical device hub.

In a twenty-eighth aspect, the present disclosure includes a connector assembly according to any of the twenty-first through twenty-seventh aspects, wherein the connector assembly is configured to deliver radioembolization fluids, chemoembolization fluids, bland embolization fluids, scout doses, or combinations thereof.

In a twenty-ninth aspect, the present disclosure includes a connector assembly according to any of the twenty-first through twenty-eighth aspects, wherein the conduit lumen comprises a varying diameter along a longitudinal length of the conduit lumen.

In a thirtieth aspect, the present disclosure includes a connector assembly according to the twenty-ninth aspect, further comprising a transition coupling region positioned at an end of the conduit lumen.

In a thirty-first aspect, the present disclosure includes a connector assembly according to the thirtieth aspect, wherein the transition coupling region comprises a transition region diameter that gradually decreases between the proximal end of the delivery conduit and a diameter of the conduit lumen.

In a thirty-second aspect, the present disclosure includes a connector assembly according to twenty-ninth aspect or thirtieth aspect, wherein the transition coupling region is configured to deform around a fluid source conduit inserted therein.

In a thirty-third aspect, the present disclosure includes a connector assembly according to any of the twenty-first through twenty-eighth aspects, wherein the delivery conduit lumen comprises a constant diameter throughout a length of the delivery conduit lumen.

In a thirty-fourth aspect, the present disclosure includes a connector assembly according to the thirty-third aspect, further comprising a transition coupling region positioned at an end of the conduit lumen.

In a thirty-fifth aspect, the present disclosure includes a connector assembly according to the thirty-fourth aspect, wherein the transition coupling region comprises a transition region diameter that gradually decreases between the proximal end of the delivery conduit and a diameter of the conduit lumen.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
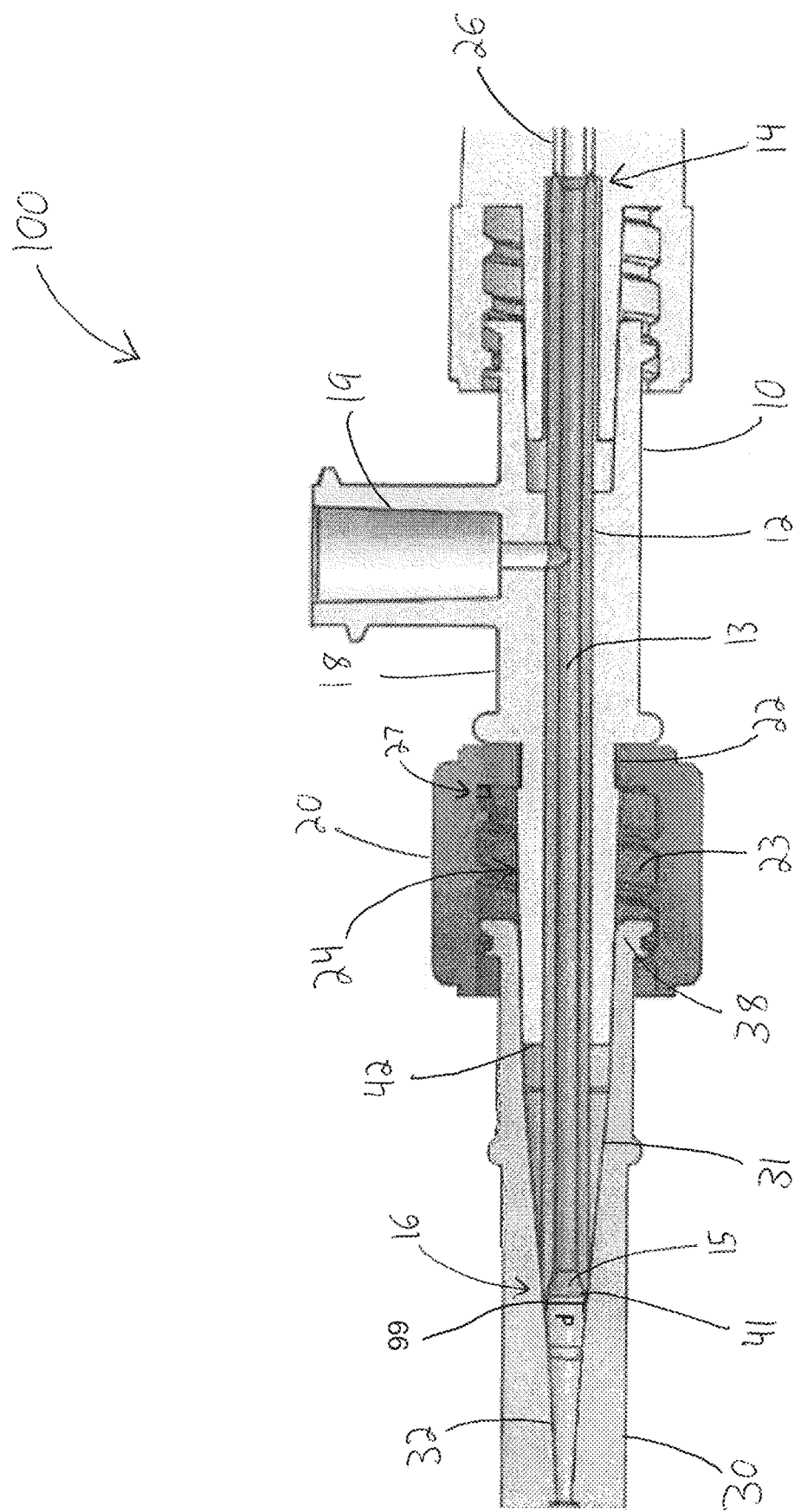
FIG. 1A schematically depicts a cross-sectional view of a connector assembly, according to one or more embodiments shown and described herein.

Connector assemblies as described herein include one or more features that result in a reduced or eliminated dead space within a fluid delivery system and/or that decrease or eliminate risks of fluid leakage from the fluid delivery system, particularly leaks that might result in exposure of medical personnel to hazardous conditions. That is, connector assemblies may connect a fluid delivery device (for example, a syringe, a needle, or generally any device capable of delivering a fluid) with a tube such as a catheter. For example, a connector assembly may include a delivery conduit and a securable connector. The delivery conduit may define a conduit lumen extending between a proximal end and a distal end of the delivery conduit. The securable connector may be configured to secure the delivery conduit to a medical device hub, such that the delivery conduit is fluidically coupled to the medical device hub. As will be described in greater detail herein, the conduit lumen may include a constant diameter region and a transition region, wherein the transition region has a gradually increasing diameter to match or approach a diameter of the medical device hub so as to decrease dead space (for example, regions wherein material may settle) within the medical device hub. In other embodiments, the conduit lumen may not include a transition region and/or a constant diameter region.

In other embodiments, a connector assembly may be used to connect two lumens having the same diameter, such that a constant diameter may be maintained from one lumen diameter to another. For example, a connector assembly may include a male connector member comprising a male locking mechanism and a stationary septum. A first conduit lumen may be securely disposed within the male locking mechanism. The connector assembly may further include a female connector member comprising a female locking mechanism, a floating septum, and a fluid delivery conduit rigidly coupled to the female locking mechanism. A second conduit lumen may be disposed within the female locking mechanism and in fluid communication with the fluid delivery conduit. The floating septum may form a seal with the female locking mechanism to prevent inadvertent leaks of fluid from the fluid delivery conduit. When assembled with the male connector member, the stationary septum may contact the floating septum and push the floating septum over the fluid delivery conduit, such that the fluid delivery conduit pierces both the floating septum and the stationary septum.

Upon release of the male connector member from the female connector member, the stationary septum and the floating septum may heal as the fluid delivery device is withdrawn to fluidically seal both the male connector portion and the female connector portion, which may prevent unintended leakage of fluid and/or particles from either the male connector member or the female connector member. Additionally, elimination or reduction of dead space within a connector assembly may lead to more efficient fluid delivery and improved treatment results. These and additional features will be discussed in greater detail with reference to the figures below.

As used herein, the term "medical device hub" describes any device that acts as a fluid port to a medical device. For example, a catheter tube may include a medical device hub or fluid port to which the connector assembly may be fluidically coupled.

As used herein, the term "fluid" may refer to a liquid and/or a liquid with particles disposed therein. For example, a fluid may include a saline carrier with a plurality of radioembolization particles dispersed, or otherwise disposed, therein. Such radioembolization particles are described subsequently in this disclosure in greater detail.

Referring to FIGS. 1A-1G and FIGS. 2A-2D, various embodiments of a connector assembly 100 are illustrated. The connector assembly 100 generally includes a delivery conduit 10 and a securable connector 20 configured to secure the delivery conduit 10 to a medical device hub 30. As will be described in greater detail herein, the connector assembly 100 connects a fluid source (for example, a syringe, needle, tube, or other reservoir) to the medical device hub 30 to provide fluid communication between the fluid source and the medical device hub 30 through the delivery conduit 10.

The delivery conduit 10 includes a proximal end 14 and a distal end 16. The proximal end 14 may be arranged to connect to one or more fluid sources and the distal end 16 may be arranged to be fluidically coupled to the medical device hub 30, as illustrated. For example, the distal end 16 may be inserted into the medical device hub 30 and contacted to a wall 31 of the medical device hub lumen 32 to provide a fluid seal therebetween. The delivery conduit 10 defines a conduit lumen 12 extending from the proximal end 14 to the distal end 16, so as to provide a fluid flow path through the conduit lumen 12. In some embodiments, the conduit lumen 12 may be integral with the delivery conduit 10 or may be a sub-component thereof (e.g., a tube).

Additionally, the delivery conduit 10 may be arranged such the delivery conduit 10 extends into the medical device hub 30 to contact or shut off against the wall 31 of the medical device hub 30. In some embodiments, the delivery conduit 10 contacts or shuts off against the wall 31 of the medical device hub 30 at two or more discrete locations and be in circumferential contact with the wall of 31 of the medical device hub 30 at that location so as to provide a fluid seal at a first contact point 42 and a second contact point distal 41 from the first contact point 42, such that possible dead space or a region which may collect fluid or particles is effectively scaled from receiving such fluid or particles.

Figure 1B:
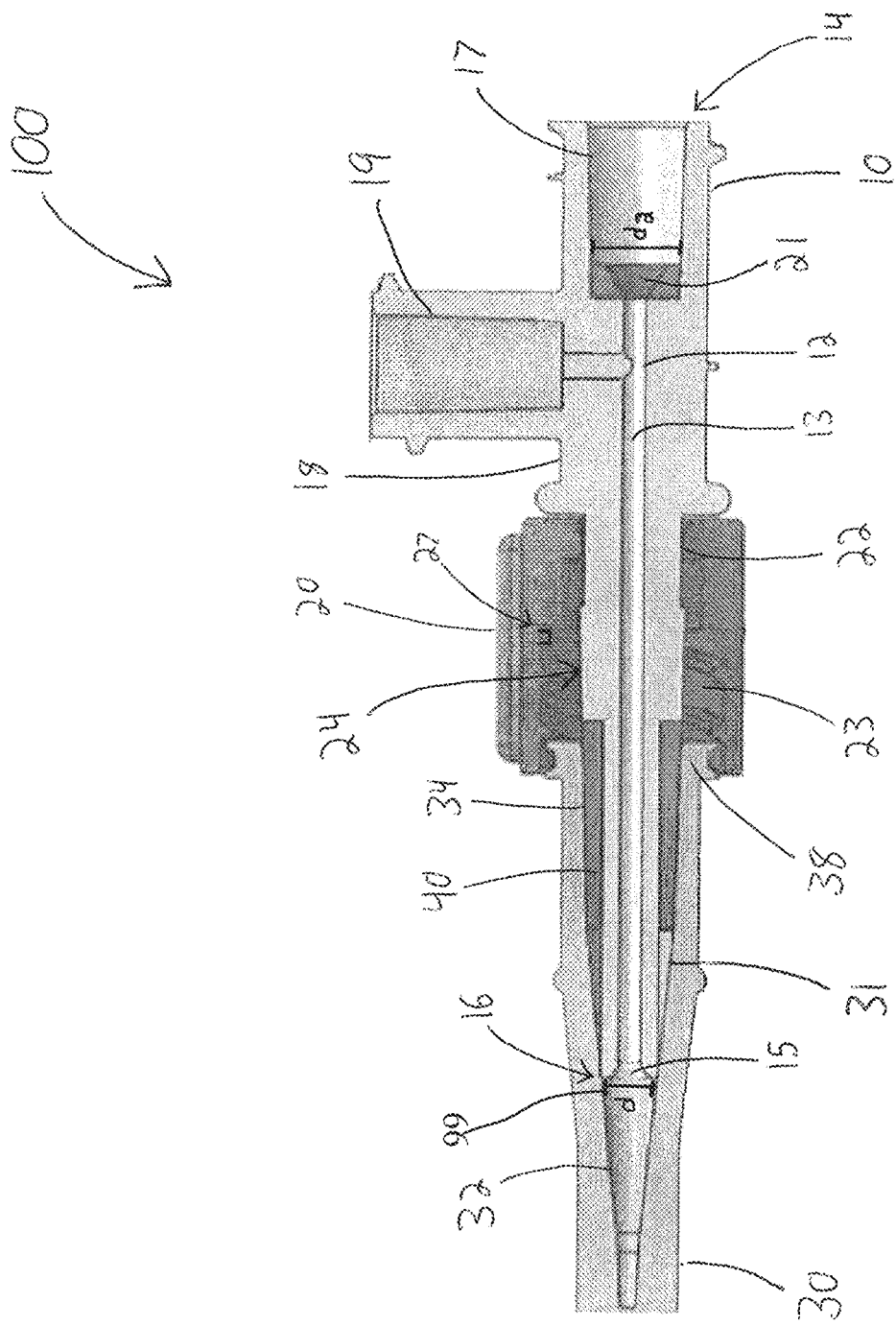
FIG. 1B schematically depicts a cross-sectional view of a connector assembly, according to one or more embodiments shown and described herein.
Figure 1C:
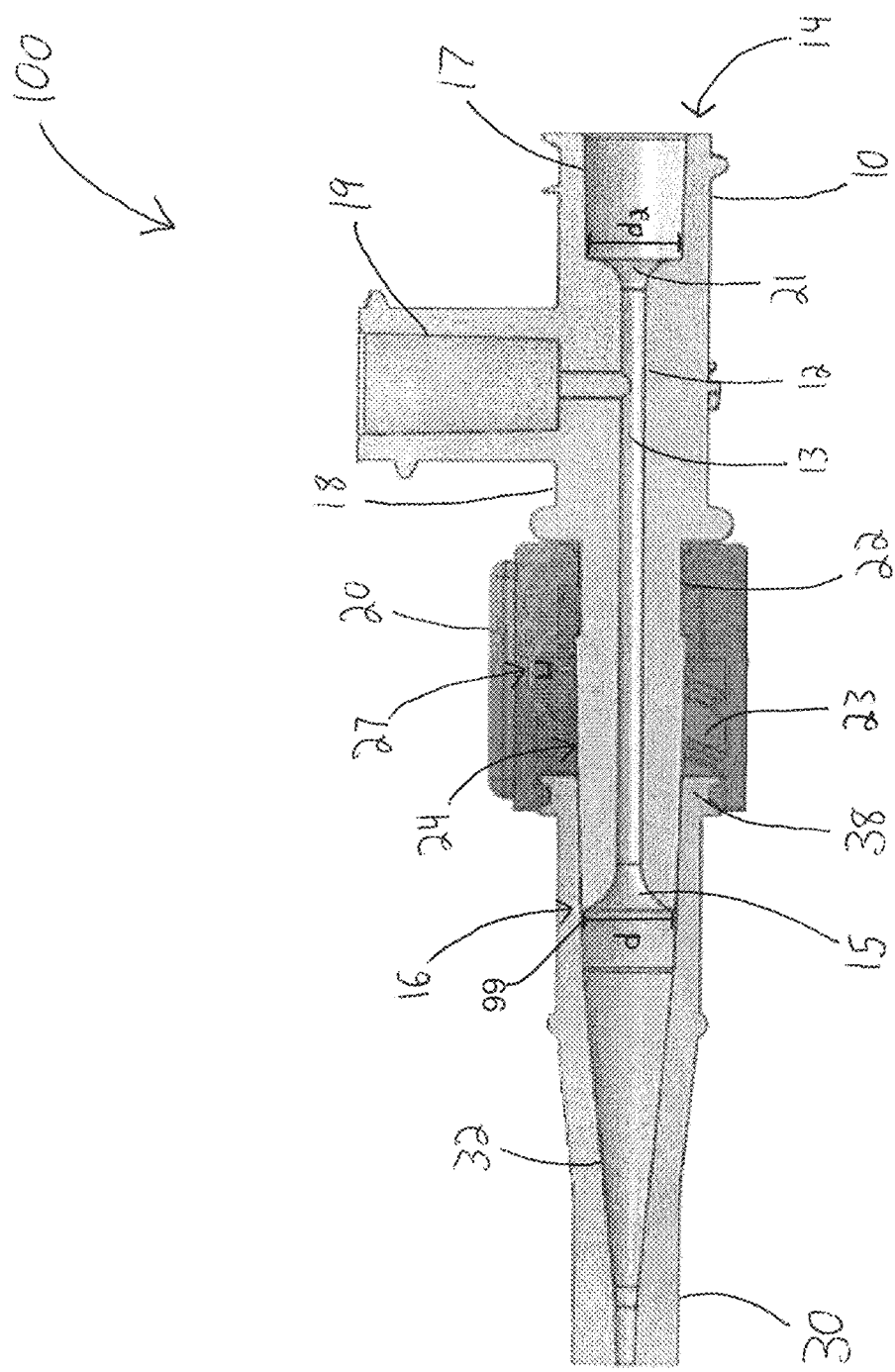
FIG. 1C schematically depicts a cross-sectional view of a connector assembly, according to one or more embodiments shown and described herein.

The conduit lumen 12 may have various configurations. For example, and as illustrated in FIGS. 1A-1C the conduit lumen 12 may include a constant diameter region 13 along a portion of the delivery conduit 10 between the proximal end 14 and the distal end 16 and a transition region 15 from the delivery conduit 10 to the distal end 16. The constant diameter region 13 may define a greater portion of the conduit lumen 12 than the transition region 15. That is, the constant diameter region 13 may extend along a length of the conduit lumen 12 for a distance greater than the transition region 15.

In some embodiments, the transition region 15 has a transition region diameter d that increases from a diameter of the constant diameter region 13 to the distal end 16 of the delivery conduit 10. For example, a leading edge 99 of the transition region 115 may be obliquely angled relative to a longitudinal axis of the conduit lumen, as depicted in FIGS. 1A-1C. In some embodiments, the leading edge 99 of the transition region 15 may be fluted (see FIG. 1B) so as to gradually increase from a diameter of the constant diameter region 13 to an internal diameter of the medical device hub 30. The transition region diameter d of the transition region 15 may be approximately equal to the diameter of the medical device hub lumen 32 at a position where the transition region 15 of the delivery conduit 10 engages the medical device hub lumen 32 of the medical device hub 30. By increasing the diameter of the transition region 15, dead space as may otherwise be caused by a sudden transition between constant diameter region 13 and the medical device hub lumen 32, may be reduced or substantially eliminated.

Referring to FIG. 1B, in some embodiments, the delivery conduit 10 includes a second transition region 21 between the proximal end 14 of the delivery conduit 10 and the constant diameter region 13. Similar to transition region 15, the second transition region 21 may include a transition region diameter $d_2$ that gradually decreases between the proximal end 14 of the delivery conduit 10 and the diameter of the constant diameter region 13. The second transition region 21 may be made from, for example, an elastomer material abutted to the constant diameter portion 13 of the delivery conduit 10. The second transition region 21 may be configured to deform around a fluid conduit inserted therein. In other embodiments, the second transition region 21 may be integral with the delivery conduit.

In some embodiments, such as illustrated in FIG. 1A, the delivery conduit 10 may not include a second transition region. Instead, the delivery conduit 10 may be abutted to a source conduit 26. The source conduit 26 by have approximately the same diameter as the conduit lumen 12 at the point of contact. For example, the source conduit 26 may have the same diameter as the constant diameter region 13.

Figure 1D:
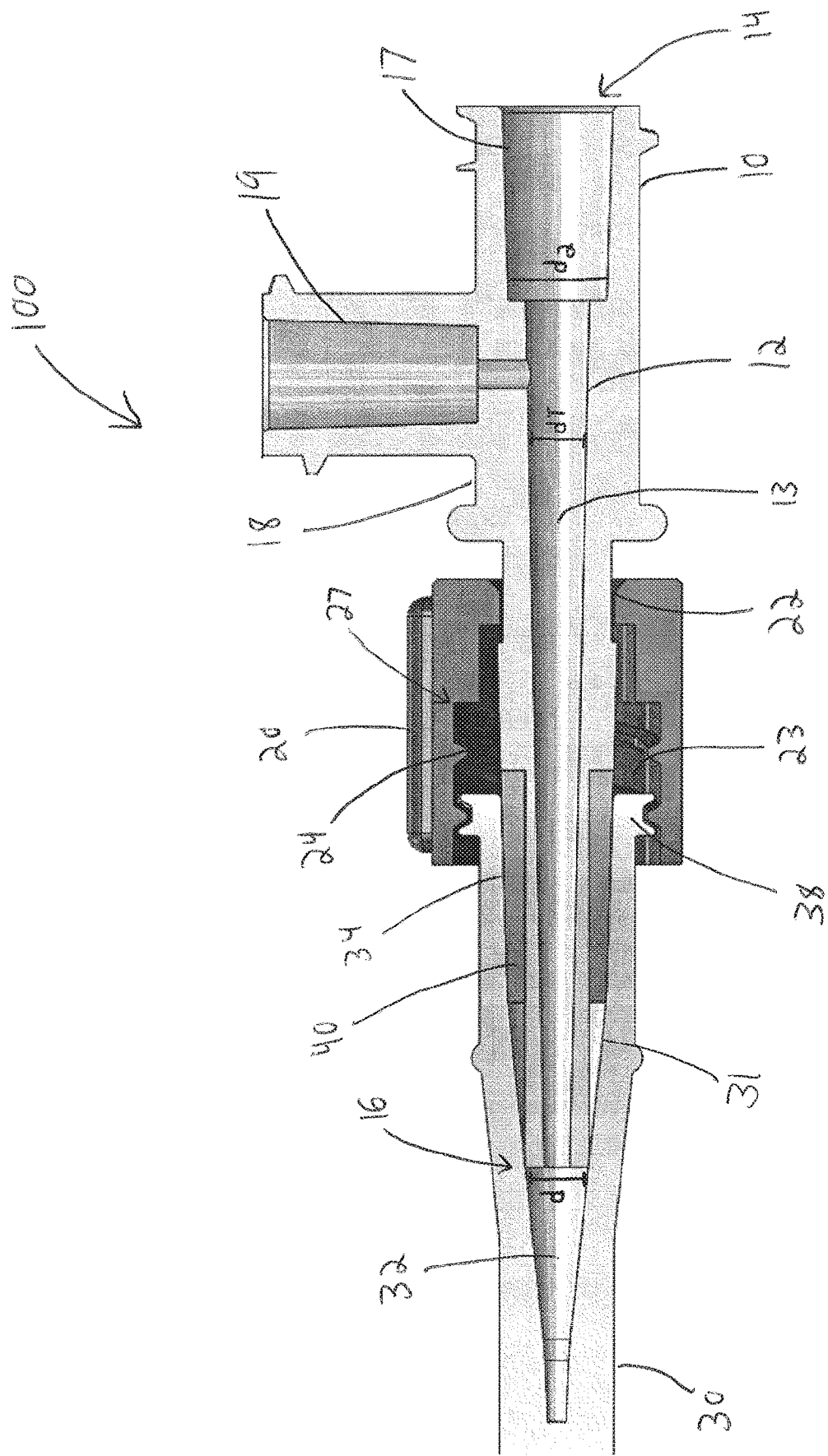
FIG. 1D schematically depicts a cross-sectional view of a connector assembly, according to one or more embodiments shown and described herein.
Figure 1H:
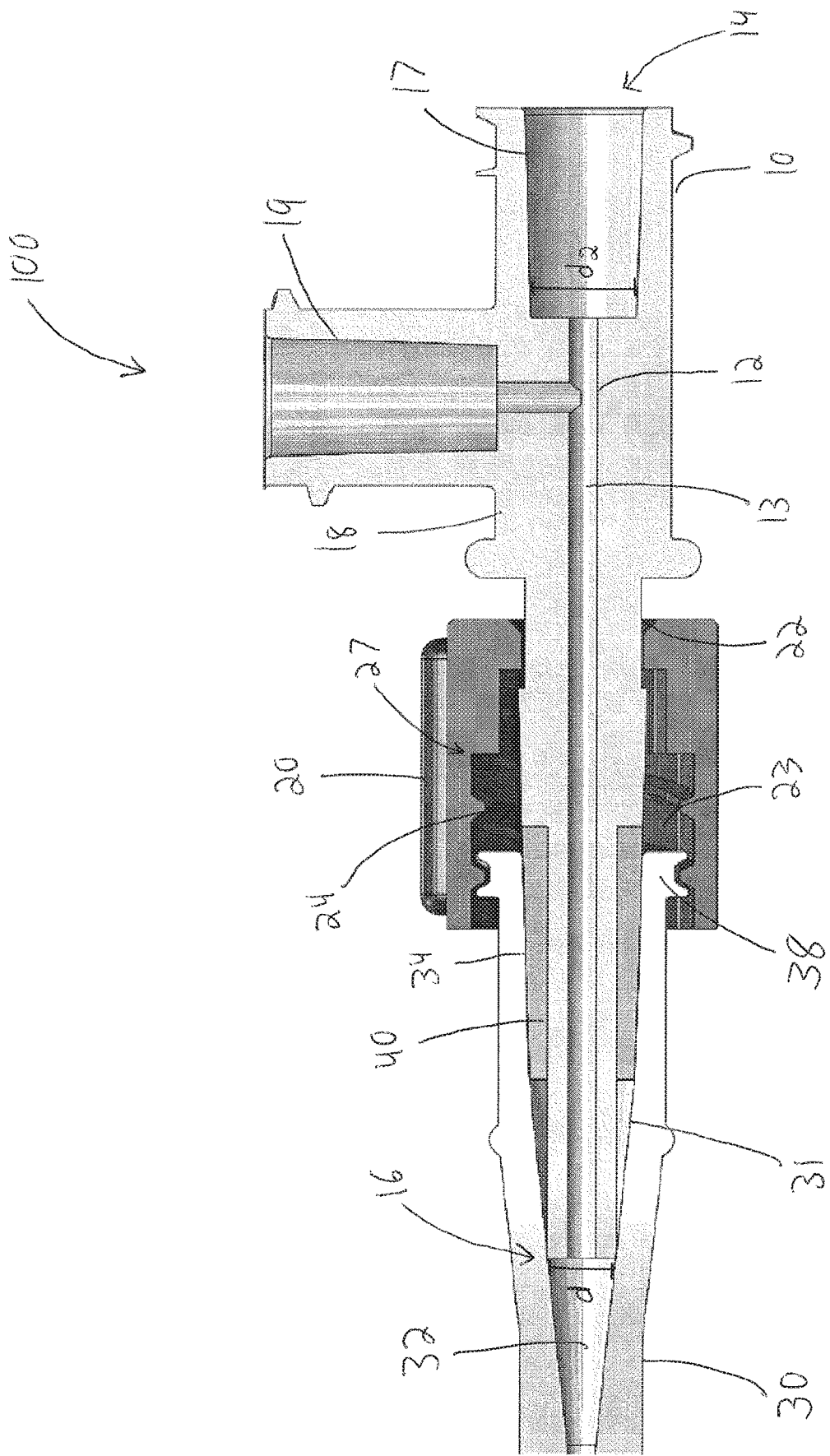
FIG. 1E schematically depicts a cross-sectional view of a connector assembly, according to one or more embodiments shown and described herein.
FIG. 1F schematically depicts a cross-sectional view of a connector assembly, according to one or more embodiments shown and described herein.
FIG. 1G schematically depicts a cross-sectional view of a connector assembly, according to one or more embodiments shown and described herein.

Referring to FIG. 1D, in some embodiments, the conduit lumen 12 may not include discrete constant diameter regions and/or transition regions. For example, and as illustrated in FIG. 1D, the conduit lumen 12 may have a varying diameter along a longitudinal length of the conduit lumen 12. In some embodiments, the conduit lumen 12 may decrease in diameter between the proximal end 14 and the distal end 16. In other embodiments, the conduit lumen 12 may increase in diameter between the proximal end 14 and the distal end 16. As illustrated in FIG. 1E, a transition coupling region 44 (similar to transition region 21) may be positioned an end of the conduit lumen 12 or integrally formed therewith. Similar to second transition region 21, the transition coupling region 44 may include a transition region diameter dr that gradually decreases between the proximal end 14 of the delivery conduit 10 and a diameter of the conduit lumen 12. The transition coupling region 44 may be made from, for example, an elastomer material abutted to the conduit lumen 12 of the delivery conduit 10. The transition coupling region 44 may be configured to deform around a fluid source conduit inserted therein. In other embodiments, the transition coupling region 44 may be integral with the delivery conduit 10.

Figure 1G:
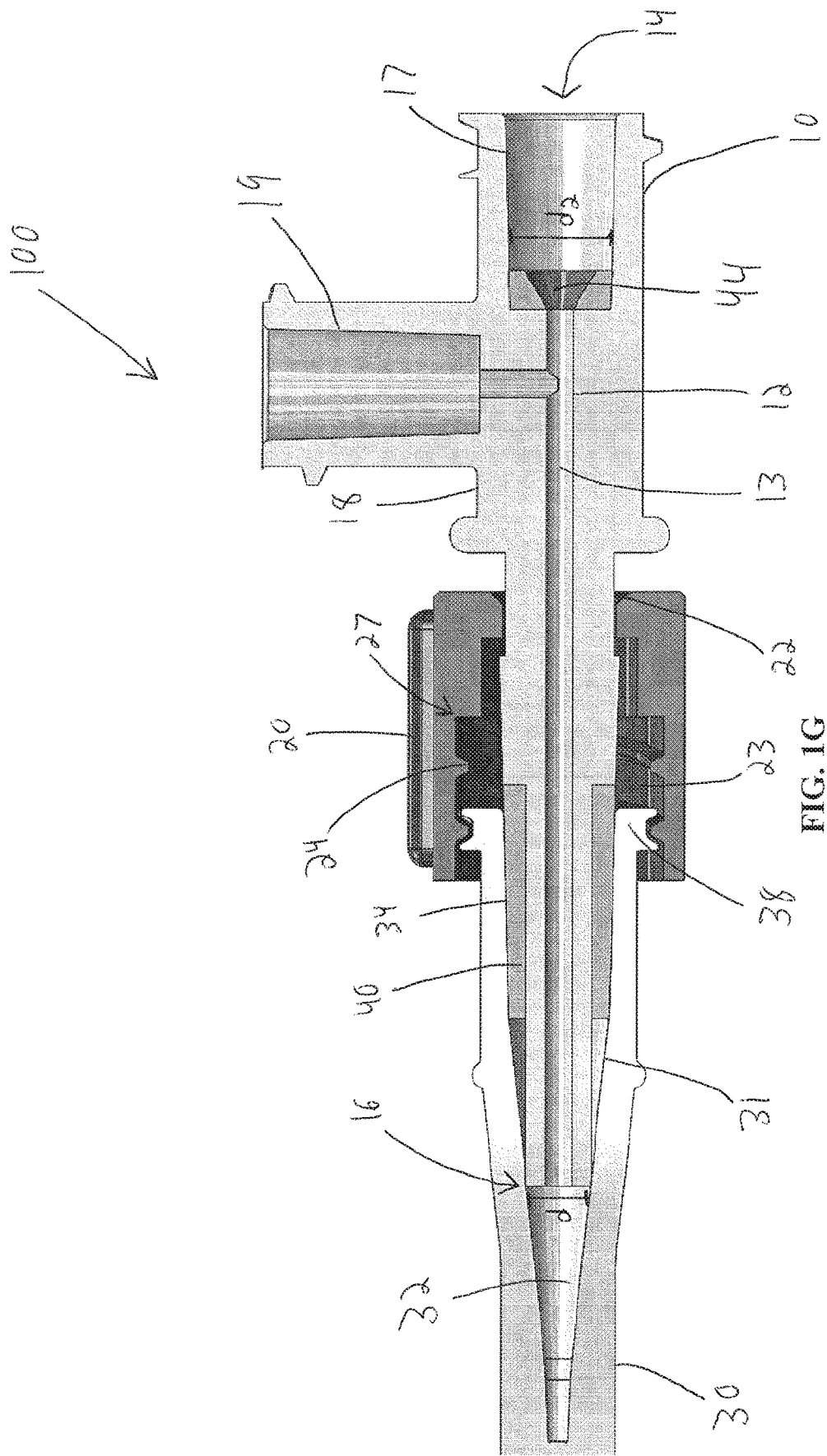

In some embodiments, such as illustrated in FIGS. 1F and 1G, the delivery conduit lumen may define a constant diameter throughout a length of the delivery conduit lumen. In some embodiments, and as illustrated in FIG. 1G, the transition region 44 may be positioned an end of the conduit lumen 12 or integrally formed therewith. In other embodiments, there may be no transition region.

In embodiments, the delivery conduit 10 includes one or more ports capable of delivering fluid from a fluid source (not shown) to the conduit lumen 12. In embodiments, for example, the delivery conduit 10 includes a first port 17 that is fluidically coupled to the conduit lumen 12 at the proximal end 14 of the delivery conduit 10. The first port 17 may be directly fluidically coupled to the constant diameter region 13 or may be fluidically coupled to the constant diameter region 13 through the second transition region 21.

Figure 2A:
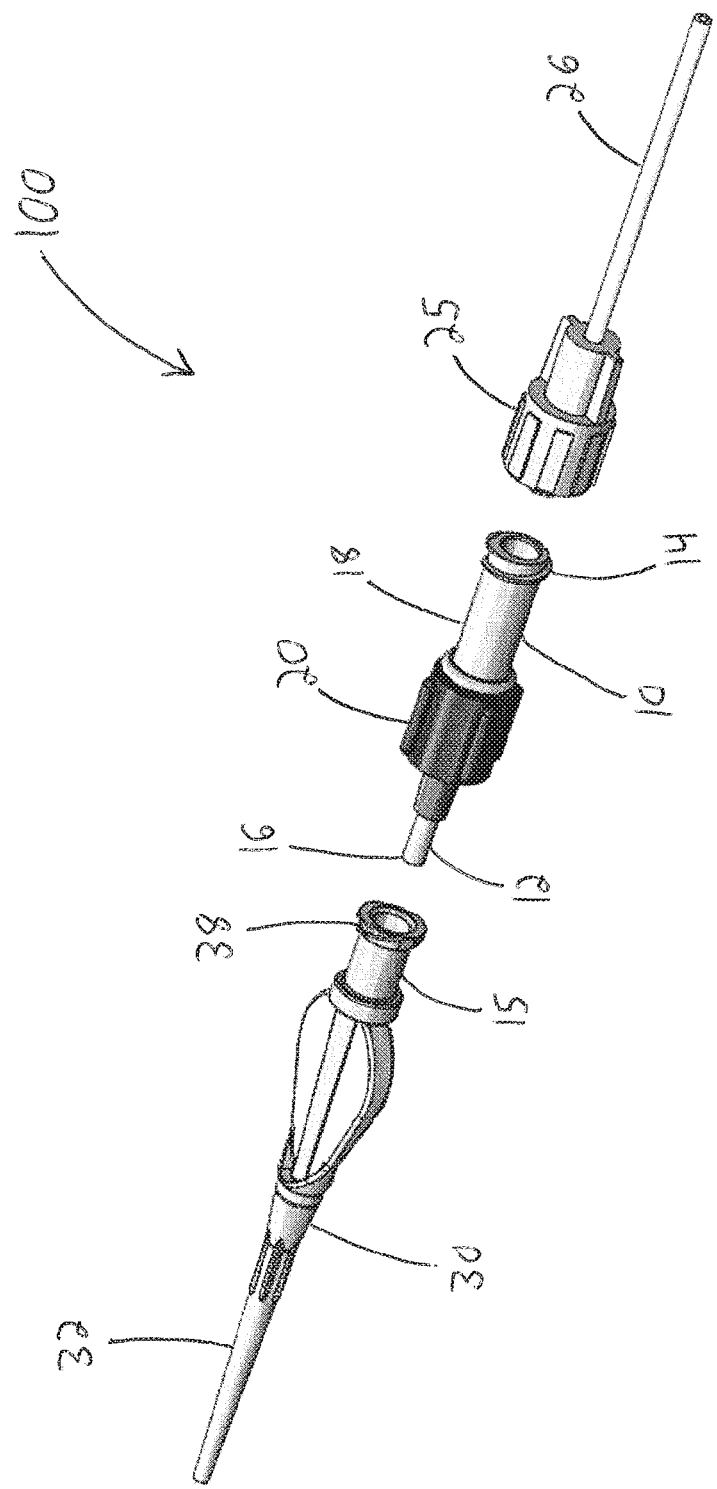
FIG. 2A schematically depicts a perspective view of a disassembled connector assembly, according to one or more embodiments shown and described herein.
Figure 2B:
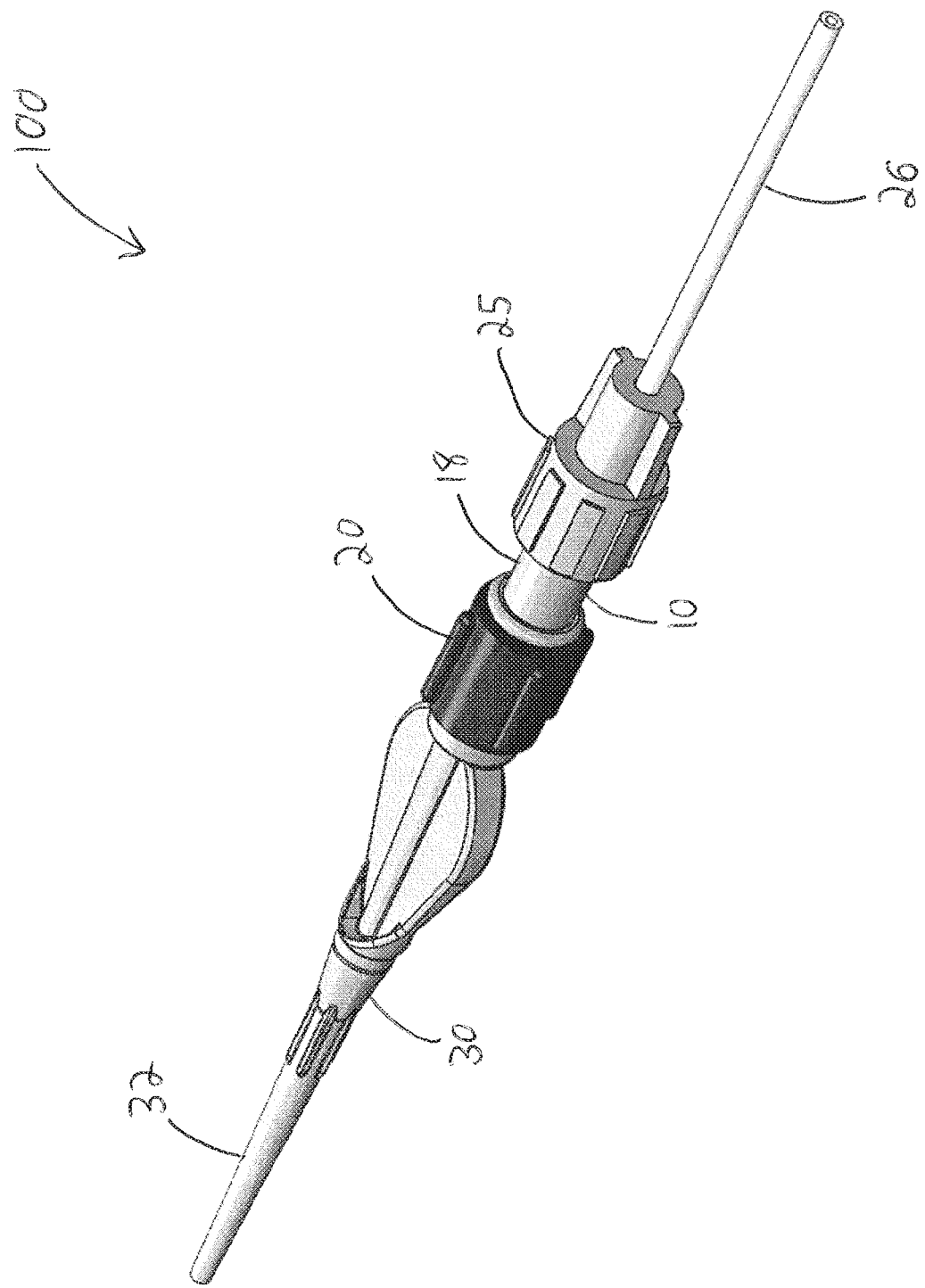
FIG. 2B schematically depicts a perspective view of an assembled connector assembly, according to one or more embodiments shown and described herein.
Figure 2C:
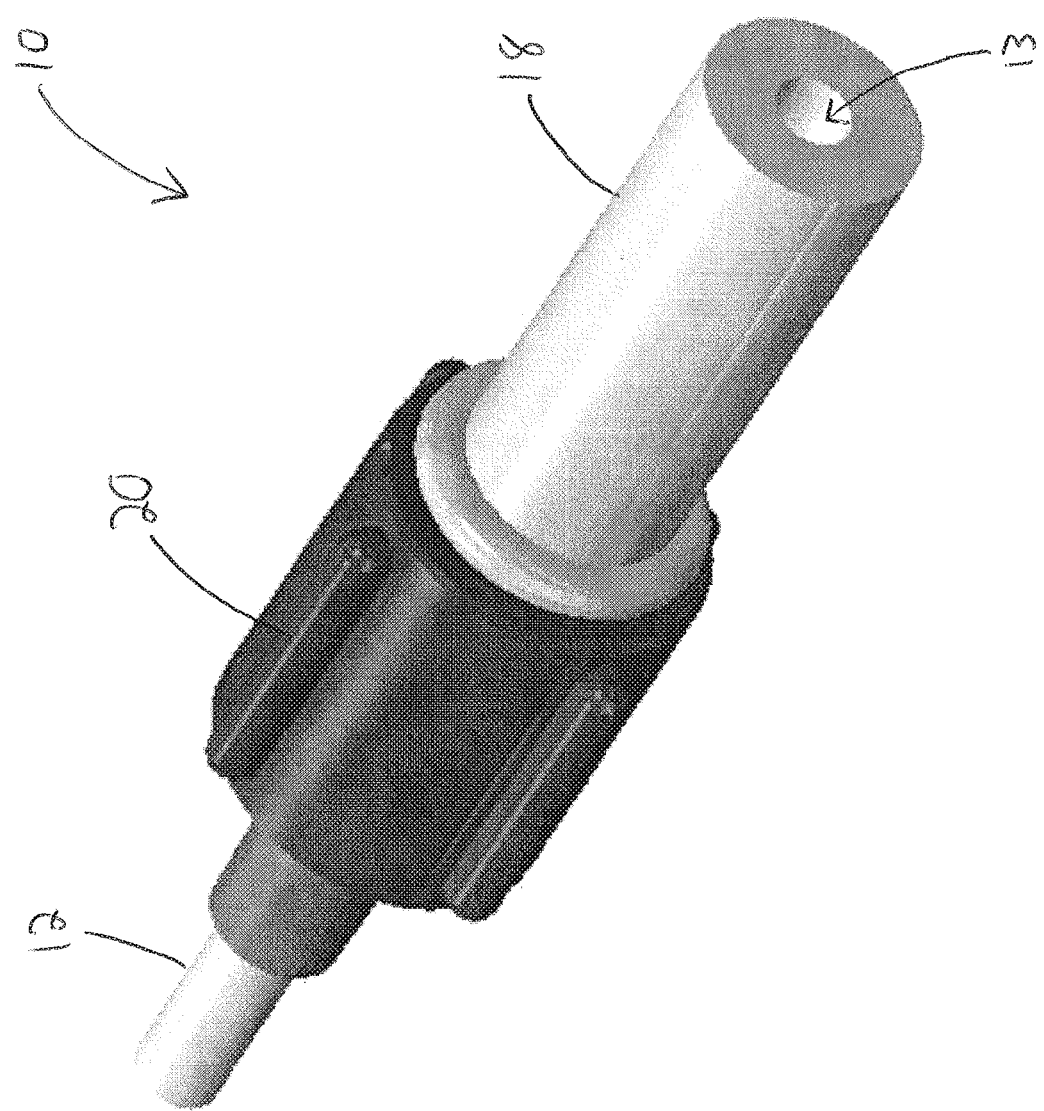
FIG. 2C schematically depicts a perspective view of a delivery conduit and a securable connector of a connector assembly, according to one or more embodiments shown and described herein.
Figure 2D:
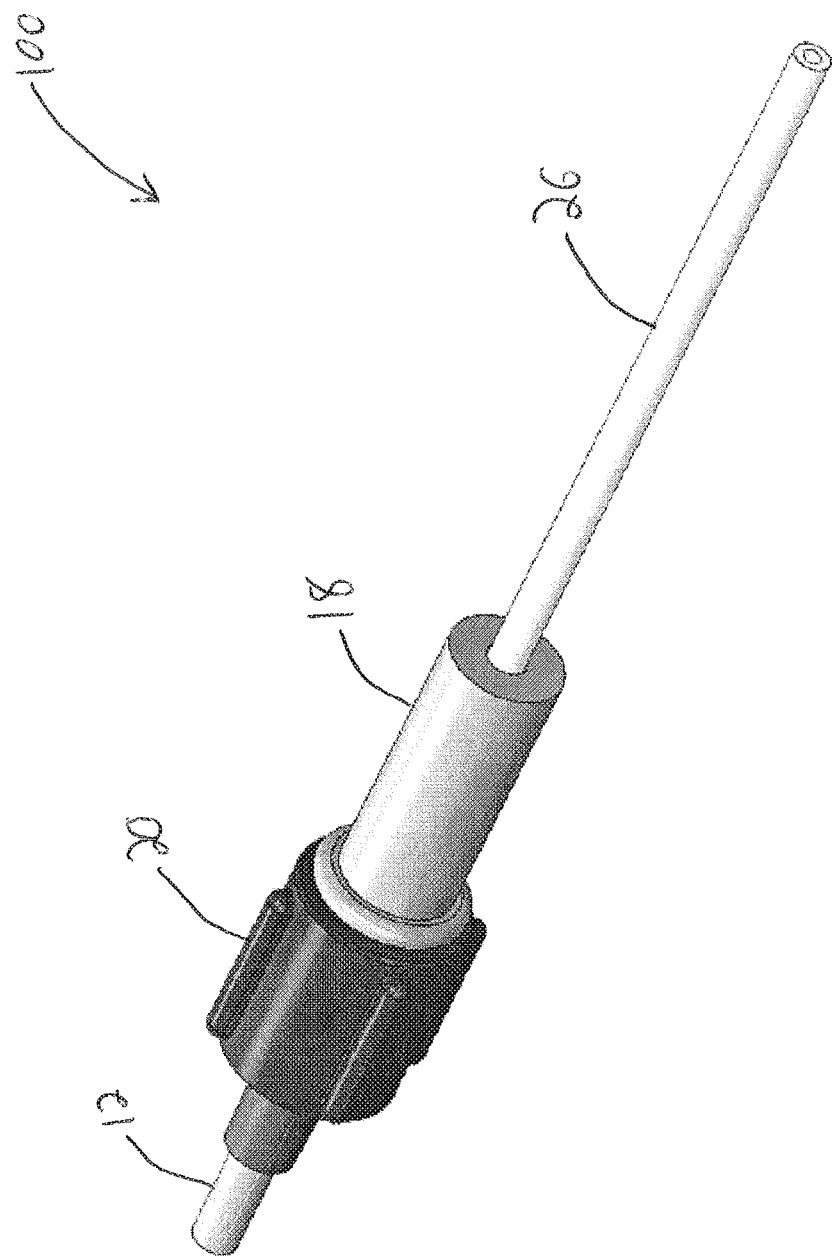
FIG. 2D schematically depicts a perspective view of the connector assembly of FIG. 2C with a conduit lumen extending therethrough.

Referring to FIGS. 2A and 2B, which illustrate a conduit having a single port 17, the fluid source may be rotatably attached to the delivery conduit 10 by a luer 25 configured to receive the port 17 positioned at the proximal end 14 of the delivery conduit 10. For example, the luer 25 may define an internal threading 23 that engages an external threading formed on the proximal end 14 of the delivery conduit 10. Engagement of luer 25 with the proximal end 14 may fluidically connect a source conduit 26, which may be fluidically coupled to the fluid source, with the conduit lumen 12. The source conduit 26, in embodiments, may be made from medical tubing. The luer 25 may be non-locking, and may be able to translate along a threaded proximal end 14 of the medical device hub 30, until the proximal end 14 contacts the source conduit 26 and/or the connection bottoms out.

Referring again to FIGS. 1A-1C, in some embodiments, the delivery conduit 10 may include a second port 19 that is also fluidically coupled to the conduit lumen 12. The second port 19 may be fluidically coupled to the constant diameter region 13 of the conduit lumen 12. The second port 19 may be oriented at a non-zero angle relative to the first port 17. For example, the second port 19, may be configured to deliver fluid into the conduit lumen 12 at an angle transverse to a fluid flow direction of the conduit lumen 12.

The first port 17, the second port 19, or any number of ports, may be capable of receiving any fluid fluidically coupled from the delivery conduit 10 to any fluid source including, but not limited to, radioembolization fluids/particles and chemoembolization fluid/particles. As noted above, the fluid source may be any vessel capable of storing fluids such as radioembolization fluids, chemoembolization fluids, bland embolization fluids, scout doses, or combinations thereof, such as a syringe, tube, or other delivery device.

The delivery conduit 10 of the connector assembly 100 may be constructed of any materials suitable for conveying a fluid through the delivery conduit 10. In particular, delivery conduits as described herein may be produced from materials that are resistant to corrosion or effects of radioembolization and/or chemoembolization fluids and/or particles such as radioactive particles, for example. For example, and not by way of limitation, the delivery conduit 10 may be formed from material including polycarbonate, polyethylene, polyethylene terephthalate, titanium, aluminum, stainless steel, copper, polyether block amide, or combinations thereof.

The connector assembly 100 may define a connector portion 24 configured to be inserted into the medical device hub lumen 32 and contact the medical device hub lumen 32 (for example, to circumferentially contact the medical device hub lumen 32). The connector portion 24 may be configured to provide an airtight and/or water tight seal between the delivery conduit 10 and the medical device hub 30. For example, insertion of the connector portion 24 into the medical device hub lumen 32 may contact and seal against the medical device hub lumen 32.

In some embodiments, an outer surface 18 of the connector portion 24 may define a recessed region 22. The recessed region 22 may extend along a portion of a length the connector portion 24. When the connector portion 24 is assembled to the medical device hub 30, the recessed region 22 may be positioned outside of the medical device hub 30. As will be described in greater detail below, the securable connector 20 may be positioned (for example, partially positioned or fully positioned) within the recessed region 22. In some embodiments, the securable connector 20 may be configured to slide along a length of the recessed region 22, such as shown in FIGS. 1B and 1C.

Referring to FIGS. 1A-1C, 2C, and 2D, the securable connector 20 may be any device configured to secure the delivery conduit 10 to the medical device hub 30. The securable connector 20 may be coupled to the outer surface 18 of the delivery conduit 10. In some embodiments, the securable connector 20 may be slidable along a portion delivery conduit 10. The securable connector 20 may configured to receive the medical device hub 30 such that the medical device hub 30 is positioned (e.g., concentrically positioned) between the surface of the delivery conduit 10 and the securable connector 20. The securable connector 20 may be secured relative to the delivery conduit 10 so as to fluidically couple the conduit lumen 12 with the medical device hub lumen 32 as defined by the medical device hub 30. The connector 20 for example, may be a rotatable connector, a snap lock, magnets, a barbed fitting, or the like.

The securable connector 20 may include any locking mechanism capable of coupling the delivery conduit 10 to the medical device hub 30. In some embodiments, the securable connector 20 may provide an airtight and/or water tight seal between the delivery conduit 10 and the medical device hub 30. In certain embodiments, the securable connector 20 is a luer locking mechanism defining the internal threading 23. The internal threading 23 may be arranged to engage a threaded end 38 located on an outer surface of the medical device hub 30. To secure the delivery conduit 10 to the medical device hub 30, the securable connector 20 may be rotated around the threaded end 38 of the medical device hub 30 so that the internal threading 23 traverses the threaded end 38 of the medical device hub 30. When removing the delivery conduit 10 from the medical device hub 30, the luer locking mechanism (securable connector 20) may then be twisted off of the medical device hub 30.

In embodiments, the securable connector 20 may include a clicking device 27 or a ratcheting mechanism (not shown) that produces an audible sound when a suitable connection is reached between the delivery conduit 10 and the medical device hub 30. The audible clicking sound may provide guidance to prevent cracks or breakages from forming in the delivery conduit 10 if a high amount of compression or torque is applied to securable connector 20. Moreover, the audible clicking sound may prevent leakages arising from too little compression or torque applied to the securable connector 20, of from an otherwise insecure connection between the delivery conduit 10 and the medical device hub 30. The clicking device 27 may include, for example, flanges or bumps formed within the securable connector 20 that are engaged with the threaded end 38 as the securable connector 20 is fastened to the threaded end 38, resulting in an audible click.

Referring again to FIG. 1B, the connector assembly 100 may include a conformable material 40 disposed between the outer surface 18 of the delivery conduit 10 and an internal surface 34 of the medical device hub 30. The conformable material 40 may provide additional sealing properties between the delivery conduit 10 and the medical device hub 30 to prevent leaks. The conformable material 40 may also provide an adjustable fitting feature, such that the connector assembly 100 may accommodate different sized medical device hubs. Suitable materials that may form the conformable material 40 may include any material capable of providing an airtight lock between the outer surface 18 of the delivery conduit 10 and the internal surface 34 of the medical device hub 30. For example, and not by way of limitation, suitable materials include a thermoplastic elastomer, a thermoplastic vulcanizate, silicone, urethane, polypropylene, or combinations thereof. It is noted that the conformable material 40 may completely encircle the connector portion 24.

As noted above, delivery devices may include catheter hubs having a lumen that is, for example, five times larger than the inner diameter of the delivery tubing (for example, the delivery conduit 10). This size difference, in the absence of the transition region 15 according to embodiments, results in the stalling of the pharmaceutical fluids that may cause particle collection in the catheter hub. During radioembolization procedures, particle collection of this kind can result in increased radioactivity in the catheter hub, thus increasing the radiation exposure risk to the patient or healthcare provider performing the procedure. Moreover, the size difference can result in an ineffective dose being delivered to the patient. The devices as provided herein decrease the amount of residual fluids that remain in the conduit lumen 12 and, thereby, may improve the efficacy and success of such treatments.

When assembled, the delivery conduit 10 is attached to the medical device hub 30, and/or any tubing, saline or contrast may be injected through the fluidically connected components to remove any air and to check for leaks around the connection. It is noted that the sizes, shapes, lengths of the inner diameters of the delivery conduit 10 and the size, shape, and length of the securable connector 20 may vary depending on the application. In some embodiments, the act of attaching the delivery conduit 10 to the medical device hub 30 may include opening a normally closed check valve or other on-off mechanism that would otherwise cause the medical device hub 30 or other tubing to be closed off any the connector assembly 100 is fully engaged.

Figure 3A:
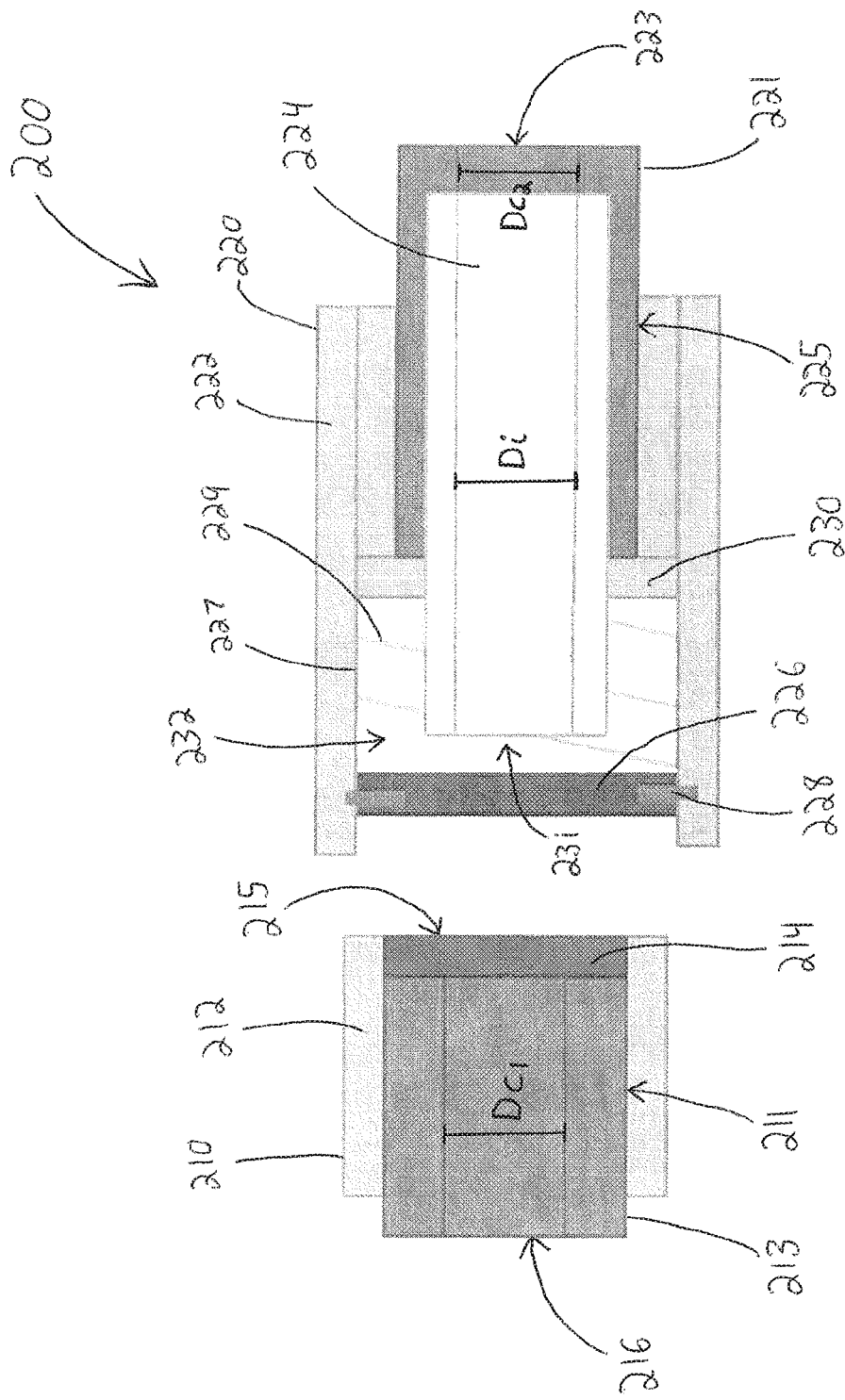
FIG. 3A schematically depicts a cross-sectional view of a connector assembly for connecting two fluid conduits, according to one or more embodiments shown and described herein.
Figure 3B:
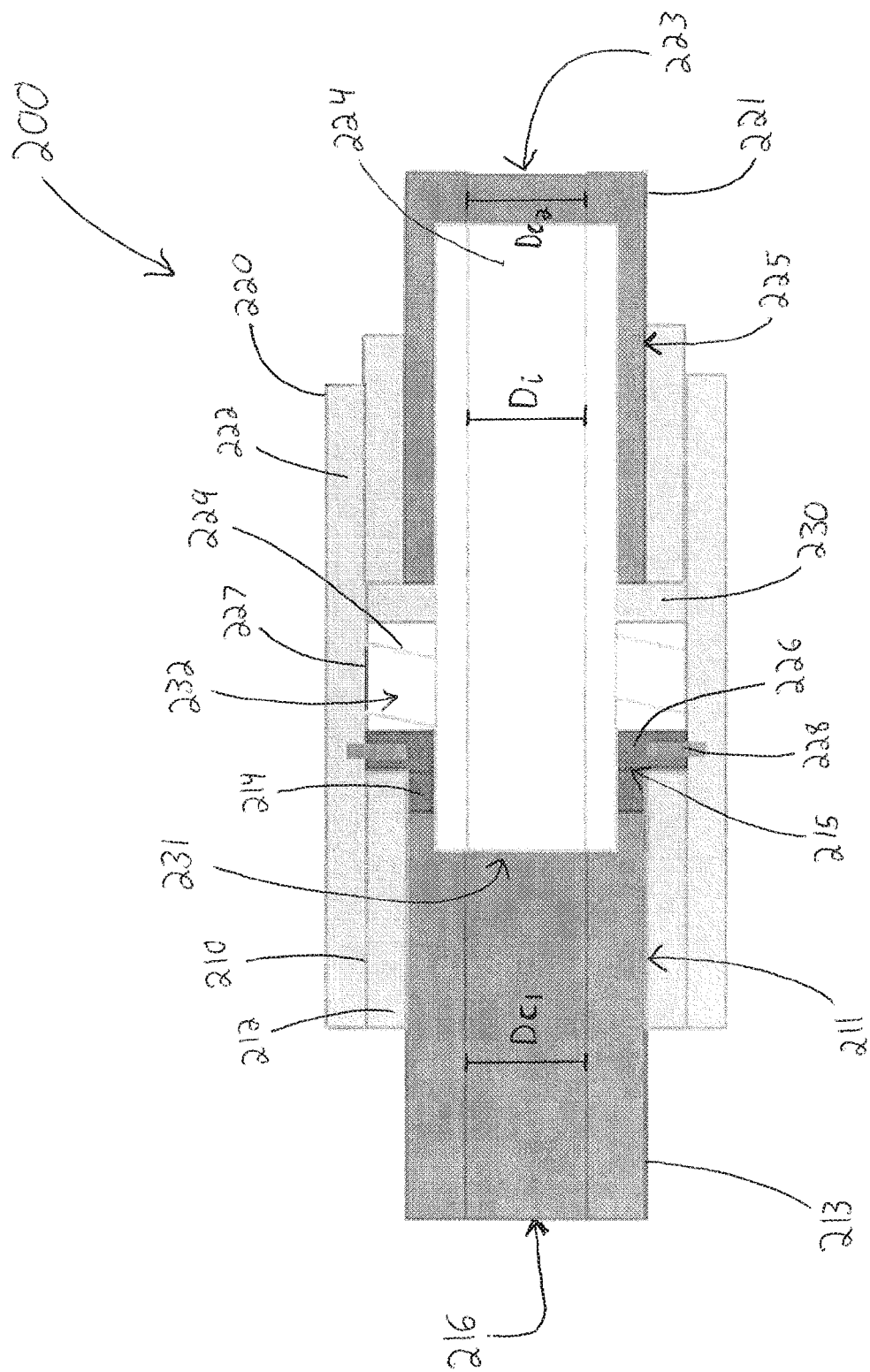
FIG. 3B schematically depicts a cross-sectional view of a connector assembly for connecting two fluid conduits, according to one or more embodiments shown and described herein.

Referring now to FIGS. 3A and 3B, other embodiments of a connector assembly 200 are schematically depicted. It is noted that the connector assembly 200 may be used to fluidically couple any fluid conduits to one another. Similar to the above embodiments, the connector assembly 200 reduces dead space or other locations of particle collection between fluid conduits to increase efficiency of medical fluid delivery.

The connector assembly 200 includes a male connector member 210 and a female connector member 220. Each of the male connector member 210 and the female connector member 220 may be mounted to a respective fluid conduit and then connected to one another to provide fluidic communication between the respective fluid conduits.

The male connector member 210 generally includes a male locking mechanism 212 and a stationary septum 214 coupled to the male locking mechanism 212. The male locking mechanism 212 may define a first conduit receiving portion 211 into which a first fluid conduit 213 may be affixed. In some embodiments, the first fluid conduit 213 may be integrally formed with the male locking mechanism 212. In other embodiments, the first fluid conduit 213 may be affixed within the first conduit receiving portion 211 by a press fit, a threaded engagement, adhesive, or the like. The first fluid conduit 213 may be inserted into the first conduit receiving portion 211 and into contact with the stationary septum 214. The first fluid conduit 213 may have a first fluid conduit lumen 216 defined through the first fluid conduit 213 for receiving a fluid flow. The first fluid conduit lumen 216 may define a first conduit diameter Dc1.

The stationary septum 214 may provide a fluid seal and/or sterile barrier between an end of the first fluid conduit 213 and the environment. The stationary septum 214 is configured so as to not move relative to the male locking mechanism 212. The stationary septum 214 may be made of a self-healing material. That is, the stationary septum 214 may be configured to reform itself and not leak after having been punctured. Such materials suitable for the stationary septum 214 may include, but are not limited to, rubber, silicone, polyisoprene, or combinations thereof. As illustrated in FIG. 3A, the stationary septum 214 may be flush with an end 215 of the male locking member 212.

The female connector member 220 may include a female locking mechanism 222, a fluid delivery conduit 224, and a floating septum 226. As will be described in greater detail herein, the female connector member 220 is configured to receive the male connector member 210 to fluidically couple the first fluid conduit 213 to a second fluid conduit 221 coupled to the female connector member 220.

The female locking mechanism 222 may define a second conduit receiving portion 225 into which the second fluid conduit 221 may be affixed. In some embodiments, the second fluid conduit 221 may be integrally formed with the female locking mechanism 222. In other embodiments, the second fluid conduit may be affixed to the second conduit receiving portion 225 by a press fit, a threaded engagement, adhesive, or the like. The female locking mechanism 222 may include a stop wall 230 to which the second fluid conduit 221 may abut. The second fluid conduit 221 may define a second fluid conduit lumen 223 extending therethrough for receiving a fluid flow. The second fluid conduit lumen may define a second conduit diameter $D_{c2}$.

The fluid delivery conduit 224 may be immovably coupled to the female locking mechanism 222. For example, and as illustrated the female fluid delivery conduit 224 may be affixed to the stop wall 230. The fluid delivery conduit 224 of the female connector member 220 may include any conduit capable of delivering fluids, specifically fluids that include particulates. These fluids may be employed in radioembolization or chemoembolization procedures. In some embodiments, the fluid delivery conduit 224 may be a needle (for example, a non-coring needle). Non-coring needles include a side opening, which may reduce the risk of ripping a hole through the stationary septum 214 and/or the floating septum 226 when the male connector member 210 becomes engaged with the female connector member 220.

The fluid delivery conduit 224 may have an internal diameter $D_i$. The internal diameter $D_i$ may be substantially equal to the first conduit diameter $D_{c1}$ and/or the second conduit diameter $D_{c2}$. In embodiments, the first fluid conduit 213 and/or the second fluid conduit 221 may be formed from a deformable material. In such embodiments, the fluid delivery conduit 224 deforms or stretches the first fluid conduit 213 and/or the second fluid conduit 221 upon engagement of the fluid delivery conduit 224 to one or both fluid conduits 213, 221. Such stretch may provide fluid-tight seal while providing a fluid flow path having a substantially contact diameter. In other embodiments, the fluid delivery conduit 224 may be molded into or positioned into a receiving channel of the second fluid conduit 221, such that the second fluid conduit 221 is configured to receive the fluid delivery conduit 224. The first fluid conduit 213 and/or the second fluid conduit 221 may be made of any suitable material, such as medical tubing. These embodiments may provide improved flow between the second fluid conduit 221 and the first fluid conduit 213, as dead space would be minimized or eliminated.

The floating septum 226 may be adjustably coupled to the female locking mechanism 222. For example, the floating septum 226 may be supported on an internal surface 227 of the female locking mechanism 222. For example, the floating septum 226 may include a flange 228 configured to engage an internal threading, groove, track, or any other suitable coupling mechanism (not shown) of the female locking mechanism 222. As the male connector member 210 is inserted into the female connector member 220, the flange 228 of the floating septum 226 may traverse the coupling mechanism of the female locking mechanism 222 to a retracted position, such as illustrated in FIG. 3B. For example, as the female locking mechanism 222 is rotated, the flange 228 of the floating septum 226 may be caused to traverse the coupling mechanism to a retracted position. The flange 228, in embodiments, may be a disk formed from any suitable material, such as plastic, capable of attaching and supporting the floating septum 226 to the female locking mechanism 222. The floating septum 226 may provide a fluid seal and/or sterile barrier to prevent fluid leakage from the female connector member 220 and to shield a user from contact with the fluid delivery conduit. The floating septum 226 may be made of a self-healing material. That is, the floating septum 226 may be configured to reform itself after having been punctured. Such material may include, but is not limited to, rubber, silicone, polyisoprene, or combinations thereof. In embodiments, the floating septum 226 and the stationary septum 214 may be made from the same or different materials.

A biasing mechanism 229 may be coupled to the floating septum 226 or integrally formed therewith and configured to bias the floating septum 226 to the extended position, as illustrated in FIG. 3A. The biasing mechanism 229 may include, but is not limited to, a compressible material, a plastic spring, a metal spring, a rubber spring, or combinations thereof. In embodiments, the biasing mechanism 229 may be disposed around the fluid delivery conduit 224 and extend between the stop wall 230 and the floating septum 226. When the floating septum 226 is depressed (for example, by the male connector member 210), the fluid delivery conduit 224 may pierce the floating septum 226 and pass therethrough. When the depressing force is removed, the floating septum 226 may again extend and heal or reseal. Accordingly, the female connector member 220 may define a first zone 232 defined by the female locking mechanism 222 and the floating septum 226 wherein the end 231 of the fluid delivery conduit 224 is contained within the first zone 232. Such containment may prevent unintended leakage from female connector member 220. In some embodiments, the floating septum 226 may be sized and shaped to extend over and seal an opening of the fluid delivery conduit 224 when in the extended position and thereby provide a fluid seal over the opening of the fluid delivery conduit 224.

In operation, the female locking mechanism 222 of the female connector member 220 may be configured to engage with the male locking mechanism 212 of the male connector member 210. Accordingly, the male connector member 210 may be fluidically coupled to an end 231 of the fluid delivery conduit 224 of the female connector member 220.

Referring to FIG. 3B, engagement of the male locking mechanism 212 and the female locking mechanism 222 moves the floating septum 226 into contact with the stationary septum 214 and causes the fluid delivery conduit 224 to pierce both the stationary septum 214 and the floating septum 226, such that the fluid delivery conduit 224 becomes inserted into the first fluid conduit lumen 216 of the male connector member 210. Accordingly, fluidic communication between the second fluid conduit 221 and the first fluid conduit 213 may be achieved through the fluid delivery conduit 224. The depression of the biasing mechanism 229 moves the floating septum 226 and the stationary septum 214 toward the fluid delivery conduit 224 of the female connector member 220 to ensure that the stationary septum 214 and the floating septum 226 are pierced when the male connector member 210 and the female connector member 220 become engaged.

As noted above, the stationary septum 214, the floating septum 226, or both, may be made from a self-healing material configured to create a seal around the fluid delivery conduit 224 as the fluid delivery conduit 224 pierces and extends through the stationary septum 214 and the floating septum 226 as the male connector member 210 engages with the female connector member 220. This may provide a fluid seal and/or sterile barrier and prevent inadvertent leakage from the connection.

As noted above, the female connector member 220 of the connector assembly 200 is configured to receive the male connector member 210 of the connector assembly 200. That is, the male locking mechanism 212 is inserted into the female locking mechanism 222 and coupled thereto. The male locking mechanism 212 and the female locking mechanism 222 may couple to one another in a twist-lock manner. For example, the male locking mechanism 212 may define an external thread and be configured to engage an internal thread of the female locking mechanism 222. In such embodiments, the female connector member 220 becomes secure around the male connector member 210 when the male connector member 210 is placed within the female connector member 220 and the female locking mechanism 222 is twisted around the male locking mechanism 212 until the components are sufficiently tightened.

The male locking mechanism 212 and/or the female locking mechanism 222 may include a clicking device or a ratcheting mechanism (not shown) that produces an audible sound when a suitable connection is reached between the two components. Specifically, the clicking device or ratcheting mechanism may produce an audible sound if too much compression or torque were applied to the locking mechanism. The audible clicking sound may prevent unnecessary cracks or breakages from forming in any of the components of the connector assembly 200 if a high amount of compression or torque is applied to the locking mechanisms. Moreover, the audible clicking sound may prevent leakages stemming from too little compression or torque applied to the male locking mechanism 212 and/or the female locking mechanism 222, thereby leading to an insecure connection between the male connector member 210 and the female connector member 220. The clicking device may include, for example flanges or bumps formed on the male locking mechanism 212 and/or the female locking mechanism 222 that are engaged when the female locking mechanism 222 is engaged with the male locking mechanism 212 resulting in an audible click. In embodiments, the male locking mechanism 212 and the female locking mechanism 222 may comprise interlocking snap locks, magnets, or barbed fittings.

The male locking mechanism 212 and the female locking mechanism 222 may be made of any suitable materials capable of providing a seal within the connector assembly 200. Further, the material may include any materials that allow for the female locking mechanism 222 to be slidably engaged with the male locking mechanism 212 when being either coupled to each other or decoupled from one another. In embodiments, the male locking mechanism 212 and the female locking mechanism 222 are formed from a material including polycarbonate, polyethylene, polyethylene terephthalate, stainless steel, aluminum, or combinations thereof. In certain embodiments, the male locking mechanism 212 and the female locking mechanism 222 are made of identical materials. The male locking mechanism 212 and the female locking mechanism 222 may further be over-molded with a material including a thermoplastic elastomer, a thermoplastic vulcanizate, silicone, urethane, polypropylene, or combinations thereof to further prevent any leakages from the connector assembly 200.

The connector assembly 200 of FIGS. 3A and 3B provide quick-scaling, continuous fluid flow paths in medical devices. This is especially beneficial when multiple fluids are needed during a medical procedure and/or when using multiple medical devices with the same fluid/delivery path. Specifically, if multiple fluids are needed during a radioembolization procedure or a chemoembolization procedure, the female connector member 220 may be quickly coupled and decoupled from the male connector member 210 depending on which fluid is needed at any given time. Moreover, the stationary septum 214 and the floating septum 226 seal any fluids in the respective portions (male and female) of the connector assembly 200, thereby decreasing a patient's or caregiver's risk of exposure to the fluids used during a radioembolization procedure or a chemoembolization procedure. Finally, the fluid delivery conduit 224 provides a consistent flow path for the fluids, which may include solid particulates and can become occluded if the provided flow path is inconsistent. The connector assembly 200 may be incorporated into any medical device to provide a consistent fluid path. For example, the connector assembly 200 may be used as a component in the connector assembly 100.

To provide for additional control of flow characteristics of the fluids traversing through the connector assembly 200, one or more components may be fluidically coupled to the fluid delivery conduit 224. Such components may include a one-way valve, a flow restrictor, a pop-off valve, or combinations thereof. These components may be placed anywhere within the male connector member 210, the female connector member 220, or combinations thereof such that the components are in fluid communication with the fluid delivery conduit 224, the first fluid conduit 213, and the second fluid conduit 221. For example, a one-way valve may be fluidically coupled to the fluid delivery conduit 224 to prevent backflow if the female connector member 220 becomes detached from the connector assembly 200. This additional component further protects the environment or persons within the environment to unintentional exposure to these fluids.

It is noted that when connection is formed, the resulting fluidically coupled system may be purged of air and/or otherwise flushed with saline and/or dye to check for leakages. Treatment of a patient by delivery of medical fluid including a therapeutic agent to the patient, for example, may then be undertaken through the connection.

Reference will now be made to therapeutic agents and microspheres comprising therapeutic agents, any of which may be delivered with or through fluid delivery systems incorporating a connector assembly according to embodiments of this disclosure.

The microspheres or "plurality of microspheres" may include multiple microspheres, embolic particles, and/or flakes which may alternatively be referred to as a "microbeads." In embodiments, the plurality of microspheres includes a therapeutic agent. In further embodiments, the plurality of microspheres may include microspheres that comprise a diamagnetic material, a therapeutic agent, a microbead material, or combinations thereof. In some embodiments, each microbead in the plurality of microspheres may include the diamagnetic material, the therapeutic agent, and the microbead material. In some embodiments, only some of the microspheres in the plurality of microspheres may include the diamagnetic material, the therapeutic agent, or a combination of the diamagnetic material and the therapeutic agent.

Individual microspheres of the plurality of microspheres may have diameters of a size suitable radioembolization medical treatment. In some embodiments, individual microspheres of the plurality of microspheres may have diameters of about 30 micrometers (μm) to about 1500 μm. In other embodiments, the individual microspheres of the plurality of microspheres may have diameters of about 30 μm to about 1500 μm, about 30 μm to about 1000 μm, about 30 μm to about 500 μm, about 30 μm to about 100 μm, about 100 μm to about 1500 μm, about 100 μm to about 1000 μm, about 100 μm to about 500 μm, about 500 μm to about 1500 μm, about 500 μm to about 1000 μm, or about 1000 μm to about 1500 μm.

The microspheres of the plurality of microspheres may include a microbead material. In some embodiments, the microbead material may include glass or silica. In other embodiments, the microbead material may include biodegradable and bioresorbable materials, which are materials that degrade and/or are reabsorbed safely within the body. Examples of biodegradable and bioresorbable materials may include, without limitation, polyglycolic acid (PGA), polyhydroxy butyrate (PHB), polyhydroxy butyrates-co-beta hydroxyl valerate (PHBV), polycaprolactone (PCL), Nylon-2. Nylon-6, polylactic-polyglycolic acid copolymers, PLGA-polyethylene glycol (PEG)-PLGA (PLGA-PEG-PLGA), carboxymethylcellulose-chitosan (CMC-CCN), chitosan, hydroxyethyl acrylate (HEA), iron-based alloys, magnesium-based alloys, and combinations thereof. In other embodiments, the microbead material may be a polymer material. In further embodiments, the microbead material may be a water-swellable polymer material, such as a polymer material capable of forming a hydrogel. The microspheres of the plurality of microspheres may have any shape common to microparticles formed from microbead material, or more specifically, a hydrogel type water-swellable polymer material. For example, the microspheres of the plurality of microspheres may be spherical or substantially spherical, may have an ovoid shape with oval-shaped or elliptical cross-sections about a longitudinal axis and circular cross-sections about an axis perpendicular to the longitudinal axis, or combinations thereof. In some embodiments, the microspheres may be porous.

In various embodiments, the microbead material may include water-swellable polymer material that includes a natural hydrogel polymer such as a chitosan or a polysaccharide, or a synthetic hydrogel polymer such as a polyacrylate, a polyamide, a polyester, a polysaccharide, a poly(methylmethacrylate), or a poly(vinyl alcohol), for example. In some embodiments, the water-swellable polymer material may be biodegradable. Specific examples of water-swellable polymer materials include, without limitation, poly(4-hydroxybutyrate), methacrylated hyaluronic acids (hyaluronic acids being polymers of disaccharides composed of D-glucuronic acid and N-acetyl-D-glucosamine), chitosan-alginates, poly(N-isopropylacrylamide) copolymers, poly(N-isopropylacrylamide)-alginates, poly(N-isopropylacrylamide)-peptides, poly(N-isopropylacrylamide)-α-acryloyloxy-β,β-dimethyl-γ-butyrolactone-hydrophilic Jeffamine, or poly(N-isopropylacrylamide)-poly(ethylene glycol) diacrylate-pentaerythritol tetrakis(3-mercapto-propionate). The microbead material may include may include water-swellable polymer materials that include derivatives of any of the foregoing materials, or may include combinations of any of the foregoing materials or their derivatives. For example, the microbead material may include a combination of multiple water-swellable polymer materials, in which each individual microbead is made of a single type of polymer, and the plurality of microspheres includes microbead materials of multiple polymer types. In some embodiments, the microbead material may include a combination of multiple water-swellable polymer materials, in which individual microspheres are composed of multiple types of polymer.

In embodiments, the individual microspheres of the plurality of microspheres may include from about 30% by weight to about 70% by weight, or from about 35% by weight to about 65% by weight, or from about 40% to about 60% by weight, or about 45% by weight to about 55% by weight, or about 50% to about 70% by weight microbead material, based on the total weight of the individual microspheres. In further embodiments, individual microspheres of the plurality of microspheres may include from about 30% by weight to about 70% by weight, or from about 35% by weight to about 65% by weight, or from about 40% to about 60% by weight, or about 45% by weight to about 55% by weight, or about 50% to about 70% by weight water-swellable polymer material, based on the total weight of the individual microspheres in the plurality of microspheres.

In embodiments, the plurality of microspheres may include one or more diamagnetic materials, which may exhibit magnetic repulsion to an external magnetic field thereby allowing the plurality of microspheres to move according to the magnetic repulsion. In some embodiments, the one or more diamagnetic materials of the plurality of microspheres may exhibit electromagnetic repulsion to an applied electrical current, an electrical field, or both, which thereby allows the plurality of microspheres to move according to the electromagnetic repulsion.

Illustrative materials that react to an electrical current or electrical field may include, but are not limited to, metals, electrolytes, superconductors, semiconductors, nonmetallic conductors, conductive polymers, shape memory polymers, and shape memory alloys. In embodiments, illustrative diamagnetic materials may include, but are not limited to, water, wood; glass; ceramics; graphite; organic compounds such as petroleum, plastic, biological tissue; and metals such as copper, mercury, gold, and bismuth. In some embodiments, the one or more microspheres may include one or more of glass, ceramics, graphite, metals, or combinations thereof. In some specific embodiments, the one or more microspheres may include one or more of graphite, bismuth, or combinations thereof.

In the microspheres of the plurality of microspheres, the one or more diamagnetic materials may be generally surrounded by the microbead material. In some embodiments, the water-swellable polymer material or some portion thereof may generally surround the one or more diamagnetic materials. In other embodiments, a microbead material shell, such as a water-soluble polymer material shell, may encapsulate a core that holds the one or more diamagnetic materials. In other embodiments, the one or more diamagnetic materials may be physically disposed within a matrix, network, or pore structure of the microbead material that may or may not have a core within an outer shell. In other embodiments, the one or more diamagnetic materials may be coated onto or otherwise chemically-bonded to the microbead material, such that the one or more diamagnetic materials have covalent chemical bonds with the microbead material.

In embodiments, the one or more diamagnetic materials may lack covalent chemical bonds with the microbead material but may in some instances interact noncovalently, ionically, or through van der Waals forces with the microbead material. For example, if the microbead material is a polymer material, the one or more diamagnetic materials may lack covalent bounds with the polymer material entirely or the microbead material may lack covalent bonds with just the polymer backbone of the polymer material. In further embodiments, the one or more diamagnetic materials may lack covalent bonds with the water-swellable polymer material entirely or the microbead material may lack covalent bonds with just the polymer backbone of the water-swellable polymer material. In further embodiments, the microbead material may generally surround the one or more diamagnetic materials, yet the one or more diamagnetic materials may be covalently bonded to a functional group of the water-swellable polymer material.

In some embodiments, one or more diamagnetic materials may be incorporated into the microspheres to produce a loaded resin material. A loaded resin material may refer to a microbead material that includes the one or more diamagnetic materials physically disposed within a matrix, network, or pore structure throughout the microsphere material. In some specific embodiments, the loaded resin material may be a graphite-loaded material or a bismuth-loaded material.

In embodiments of incorporating the one or more diamagnetic materials into the microspheres, the microspheres may have a core-shell morphology, where the shell includes the microbead material, and the core, encapsulated by the shell, includes the one or more diamagnetic materials or the loaded resin material. The term "encapsulated" broadly includes embodiments for which the shell or some portion thereof generally surrounds the core. In some specific embodiments, where the microspheres have a core-shell morphology, the shell includes polycarbonate or nylon, and the core includes the loaded resin material. In other embodiments, the one or more diamagnetic materials or the loaded resin material may be the core material encapsulated in a biocompatible resin shell. Examples of the biocompatible resin may include, without limitation, epoxy resins, polyether ether ketone resins, high-density polyethylenes, or combinations thereof. In some embodiments, the biocompatible resin material may be used to separate the one or more diamagnetic materials or the loaded resin material from one or more other functional layers in the microbead. The microspheres having a core-shell morphology may be produced by a microfluidic manufacturing process. In other embodiments, the loaded resin material may be physically disposed within a matrix, network, or pore structure of the microbead material that may or may not have a core within an outer shell.

In embodiments, the plurality of microspheres may include one or more drug-loaded microspheres. In some embodiments, the plurality of microspheres may be entirely made up of drug-loaded microspheres, where each microbead also includes a diamagnetic material. In other embodiments, the plurality of microspheres may include a mixture of drug-loaded microspheres and microspheres that include a diamagnetic material.

In embodiments, the drug-loaded microspheres may be microspheres loaded with a therapeutic agent or with a complex of a therapeutic agent and a carrier. Individual drug-loaded microspheres of the plurality of microspheres may include one therapeutic agent or a plurality of therapeutic agents. Collectively, the microspheres of the plurality of microspheres may include some drug-loaded microspheres loaded with one specific therapeutic agent or a combination of specific therapeutic agents and other microspheres loaded with a different specific therapeutic agent or combination of specific therapeutic agents.

In some embodiments, the therapeutic agent may be a hydrophilic therapeutic agent, a water-soluble therapeutic agent, or a therapeutic agent that has at least some solubility in an aqueous solution. In some embodiments, the therapeutic agent may be a chemotherapeutic agent having at least some efficacy for treating a disease such as cancer. In some embodiments, the therapeutic agent may be a chemotherapeutic agent having at least some efficacy for treating a cancer such as hepatocellular carcinoma, liver cancer, prostate cancer, or breast cancer. The therapeutic agent may have one or more chemical moieties or atomic centers having a positive or negative charge or affinity. Examples of specific therapeutic agents may include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel.

In some embodiments, the therapeutic agent may be a radiotherapeutic agent having at least some efficacy for treating a disease such as cancer. In some embodiments, the therapeutic agent may be a radiotherapeutic agent having at least some efficacy for treating a cancer such as hepatocellular carcinoma, liver cancer, prostate cancer, or breast cancer. The radiotherapeutic agent may include a radioisotope such as a beta-gamma emitter that emits sufficient gamma radiation to enable imaging. Examples of specific radiotherapeutic agents include, without limitation, bismuth-213, boron-10, cesium-131, cesium-137, cobalt-60, dysprosium-165, erbium-169, holmium-166, iodine-125, iodine-131, iridium-192, iron-59, lead-212, lutetium-177, molybdenum-99, palladium-103, phosphorus-32, potassium-42, radium-223, rhenium-186, rhenium-188, samarium-153, selenium-75, sodium-24, strontium-89, technetium-99m, thorium-227, xenon-133, ytterbium-169, ytterbium-177, and yttrium-90. Some other examples include actinium-225, astatine-211, bismuth-213, carbon-11, nitrogen-13, oxygen-15, fluorine-18, cobalt-57, copper-64, copper-67, fluorine-18, gallium-67, gallium-68, germanium-68, indium-111, iodine-123, iodine-124, krypton-81m, rubidium-82, strontium-82, and thallium-201. In some specific embodiments, the plurality of microspheres may include drug-loaded microspheres comprising yttrium-90.

In some embodiments, the water-swellable polymer material or some portion thereof generally surrounds the therapeutic agent or the complex including the therapeutic agent. In some embodiments, a water-soluble polymer material shell may encapsulate a core that holds the therapeutic agent or complex. In other embodiments, the therapeutic agent or the complex may be physically disposed within a matrix, network, or pore structure of a water-swellable polymer material that may or may not have a core within an outer shell.

In some embodiments, the therapeutic agent of the drug-loaded microbead may generally surround the microspheres of the microbead material but lack of covalent chemical bonds between the therapeutic agent and the microbead material. Despite lacking covalent chemical bonds, the therapeutic agent and microbead material may have noncovalent intermolecular interactions such as ionic interactions or a van der Waals interaction. In some embodiments, the therapeutic agent of the drug-loaded microbead may generally surround the microbead material and lack covalent chemical bonds to the polymer backbone water-swellable polymer material, yet the therapeutic agent may be chemically bonded to a functional group of the water-swellable polymer material. In some embodiments, the therapeutic agent is not chemically bonded to the water-swellable polymer material at all.

The drug-loaded microspheres may include an amount of therapeutic agent that has a desired therapeutic effect or activity, based on the intended use for the plurality of microspheres and the particular therapeutic agent present in the individual microspheres. The amount of therapeutic agent in the individual drug-loaded microspheres of the plurality of microspheres may be adjusted through particular techniques involved during drug loading, such as loading time, loading temperature, or concentration of therapeutic agent in a loading solution, for example. The amount of therapeutic agent in the individual drug-loaded microspheres of the plurality of microspheres may be adjusted through synthetic techniques involved for synthesizing the microspheres themselves, such as through adjusting polymer molecular weights, degree of hydrogel crosslinking, polymer density, or polymer porosity of the water-swellable polymer material. For example, when doxorubicin is the therapeutic agent, the amount of drug loading in the drug-loaded microspheres may be adjusted with respect to the number of negative charges in the polymer backbone of the water-swellable polymer material. Similarly, when sorafenib is the therapeutic agent, the sorafenib may be embedded within polymeric micelles or liposomes that may be embedded within the microbead structure. In some embodiments, the amount of therapeutic agent in the individual microspheres of the drug-loaded microspheres may be adjusted through choice of the carrier.

In some embodiments, when the therapeutic agent is a radiotherapeutic agent, the radiotherapeutic agent may be loaded into the microspheres by a precipitation method. For example, when yttrium-90 is the therapeutic agent, such precipitation methods may include preparing a solution of soluble yttrium salt (e.g., $YCl_3$) for which at least a portion of the yttrium is yttrium-90, chemically converting the soluble salt to small precipitates of an insoluble salt such as yttrium phosphate ($YPO_4$), adding microspheres to solution containing the precipitates, and causing the yttrium phosphate to nucleate onto the surfaces of the beads and, if the microbead is porous, into at least some of the pores. In another example, such precipitation methods may include adding microspheres to a solution of soluble yttrium (e.g., $YCl_3$) for which at least a portion of the yttrium is yttrium-90, allowing the soluble yttrium to penetrate into the pores of the microspheres, and then converting the soluble yttrium to insoluble yttrium, which may include yttrium phosphate ($YPO_4$), yttrium sulfate ($Y_2(SO_4)_3$), and yttrium carbonate ($Y_2(CO_3)_3$). In another example, yttrium-90 may be bonded to or coated onto surfaces of the microbead.

In example embodiments, the individual microspheres of the plurality of microspheres may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight therapeutic agent, based on the total weight of the individual microspheres in the plurality of microspheres.

In some embodiments, the drug-loaded microbead may include a complex of a carrier and a therapeutic agent. In the complex, the therapeutic agent may be chemically bonded to the carrier or may be associated with the carrier by a non-covalent means such as encapsulation or a van der Waals interaction. In embodiments, the complex may be embedded within the microbead material. In further embodiments, the complex may be embedded within the water-swellable polymer material. When the complex is embedded within the microbead material, the carrier may be chemically bonded to the microbead material while the therapeutic agent is not chemically bonded to the microbead material. Without intent to be bound by theory, it is believed that when the therapeutic agent is bonded or associated with the carrier but is not chemically bonded to the microbead material, the drug-loaded microspheres of the plurality of microspheres may be less susceptible to shrinking as a result of replacing water molecules with drug molecules during drug loading. Accordingly, the final size distribution of the drug-loaded microspheres may be controlled more readily by selecting appropriate microbead sizes before the therapeutic agent is loaded.

In embodiments in which the drug-loaded microbead includes a complex of the carrier and the therapeutic agent, the carrier may be any pharmaceutically-acceptable compound that can complex with or encapsulate the therapeutic agent. In some embodiments, the carrier may have charged chemical groups or chemical groups with dipole moments that interact with corresponding chemical groups of the therapeutic agent having an opposite charge or opposite dipole moment. If the carrier is a polymeric material, the carrier may be a different material from the water-swellable polymer material. Non-limiting examples of suitable carriers include polysaccharides, liposomes, polymeric micelles, Pluronics, polycaprolactone-b-methoxy-PEG, poly(aspartic acid)-b-PEG, poly(benzyl-L-glutamate)-b-PEG, poly(D,L-lactide)-b-methoxy-PEG, poly(β-benzyl-L-asparate)-b-PEG). Non-limiting examples of polysaccharides include dextrans and dextran sulfates such as dextran sodium sulfate. In one example embodiment, the carrier may include a dextran sodium sulfate having a weight-average molecular weight of from about 40 kDa (kilodalton) to about 500 kDa, or from about 50 kDa to about 300 kDa, or from about 100 kDa to about 300 kDa, or about 100 kDa to about 200 kDa.

In example embodiments, the individual microspheres of the plurality of microspheres may include from about 1% by weight to about 40% by weight, or from about 1% by weight to about 30% by weight, or from about 1% by weight to about 25% by weight, or from about 1% by weight to about 20% by weight, or from about 5% by weight to about 40% by weight, or from about 10% by weight to about 40% by weight, or from about 20% by weight to about 40% by weight carrier, based on the total weight of the individual microbead in the plurality of microspheres.

In example embodiments, the individual microspheres of the plurality of microspheres include water. In example embodiments, the individual microspheres of the plurality of microspheres according to embodiments may have a low water content such as less than 1% by weight, or less than 0.5% by weight, or less than 0.1% by weight, or less than 0.05% (500 ppm) by weight, or less than 0.02% (200 ppm) by weight, or less than 0.01% (100 ppm) by weight, or less than 0.005 (50 ppm) by weight, or less than 0.002% (20 ppm) by weight, or less than 0.001% (10 ppm) by weight water, based on the total weight of the individual microspheres. Without intent to be bound by theory, it is believed that a low water content of the microbead increases the shelf-life and long-term stability of the microbead. Further, it is believed that water contents significantly greater than 1% by weight (such as 2%, 3%, 5%, or 10%, for example) based on the total weight of the microbead, may lead to decomposition or hydrolysis of the therapeutic agent, instability or breaking apart of the water-swellable polymer, or a combination of these, within a few days or even a few hours, such that the microbead cannot be used for embolization procedures, even if the microbead is rehydrated. It is believed that the shelf-life and long-term stability of having water contents significantly greater than 1% by weight are not sufficiently long to ensure viability of the therapeutic agent over the time period from manufacture of the microbead to use of the in an embolization procedure. It is believed that selection of the water-swellable polymer material may correlate with the ability for water to be removed from the microspheres by lyophilization or other drying technique or combination of drying techniques in an amount sufficient to prevent decomposition of the therapeutic agent.

A low water content of the microbead, as previously described, may be attained by drying techniques. In this regard, the microspheres may be dry or nearly dehydrated compositions of the microspheres containing the embedded therapeutic agent or the embedded complex of the therapeutic agent and the carrier. The microspheres may have a powder-like consistency. Accordingly, the microspheres may be made suitable for injection into a subject being treated by rehydrating the microspheres so that the plurality of microspheres may be suitable for embolization. Regardless, the microspheres may be provided in such a form that a physician needs to add only an aqueous solution such as water or physiologically buffered saline solution to the plurality of microspheres to prepare the plurality of microspheres for use in an embolization procedure.

It is noted that terms like "typically." when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the term "approximately" is utilized herein to represent the inherent degree of uncertainty that may be attributed to any quantitative comparison, value, measurement, or other representation. The term "approximately" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A connector assembly comprising:
   a delivery conduit defining a lumen extending between a proximal end and a distal end,
   a tube positioned within the lumen of the delivery conduit and defining a conduit lumen, and
   a securable connector configured to secure the delivery conduit to a medical device hub defining a medical device hub lumen and an internal surface, wherein:
   the conduit lumen comprises a constant diameter region along a portion of the delivery conduit between the proximal end and the distal end and a transition region from the delivery conduit to the distal end, wherein:
     a leading edge of the transition region is obliquely angled relative to a longitudinal axis of the conduit lumen
     a transition region diameter of the transition region increases from the constant diameter region to the distal end of the delivery conduit, such that the transition region has a bell shaped taper and the transition region diameter is configured to be approximately equal to a diameter of the medial device hub lumen at a position where the transition region engages the medical device hub;
   the securable connector is coupled to an outer surface of the delivery conduit and is slidable along a portion thereof;
   the securable connector is configured to receive the medical device hub such that the medical device hub is positioned between the surface of the delivery conduit and the securable connector; and
   the securable connector is secured relative to the delivery conduit so as to fluidically couple the conduit lumen with the medical device hub lumen.

2. The connector assembly of claim 1, further comprising a conformable material configured to be disposed between the outer surface of the delivery conduit and the internal surface of the medical device hub.

3. The connector assembly of claim 2, wherein the conformable material comprises a thermoplastic elastomer, a thermoplastic vulcanizate, silicone, urethane, polypropylene, or combinations thereof.

4. The connector assembly claim 1, wherein the delivery conduit comprises a first port fluidically coupled to the constant diameter region of the conduit lumen; and a second port fluidically coupled to the constant diameter region of the conduit lumen at a non-zero angle relative to the first port.

5. The connector assembly of claim 1, wherein the delivery conduit comprises a second transition region extending between the proximal end of the delivery conduit and the constant diameter region, wherein the second transition region comprises a transition region diameter that gradually decreases from the proximal end of the delivery conduit to the constant diameter region.

6. The connector assembly of claim 1, wherein the delivery conduit is formed from a material comprising polycarbonate, polyethylene, polyethylene terephthalate, titanium, aluminum, stainless steel, copper, polyether block amide, or combinations thereof.

7. The connector assembly of claim 1, wherein the outer surface of the delivery conduit defines a recessed region, and the securable connector is positioned within the recessed region and configured to slide along a length of the recessed region.

8. The connector assembly of claim 1, wherein the securable connector comprises a luer locking mechanism comprising an internal thread configured to receive an external thread located on an outer surface of the medical device hub.

9. The connector assembly of claim 1, wherein the connector assembly is configured to deliver radioembolization fluids, chemoembolization fluids, bland embolization fluids, scout doses, or combinations thereof.

10. The connector assembly of claim 1, further comprising the medical device hub.

11. The connector assembly of claim 1, wherein an interface of the transition region and the medical device hub is configured to prevent the formation of turbulent flow at a distal end of the transition region.

12. The connector assembly of claim 1, wherein the entire transition region has a non-linear taper.

13. The connector assembly of claim 1, wherein the delivery conduit contacts a wall of the of the medical device hub at two or more discrete locations and wherein the delivery conduit is spaced away from the medical device hub between the two or more discrete locations.

14. A connector assembly comprising:
   a delivery conduit defining a lumen extending between a proximal end and a distal end,
   a tube positioned within the lumen of the delivery conduit and defining a conduit lumen, and
   a securable connector configured to secure the delivery conduit to a medical device hub defining a medical device hub lumen and an internal surface, wherein:
   the conduit lumen comprises a constant diameter region along a portion of the delivery conduit between the proximal end and the distal end and a transition region from the delivery conduit to the distal end;

a transition region diameter of the transition region increases from the constant diameter region to the distal end of the delivery conduit, such that the transition region diameter is configured to be approximately equal to a diameter of the medial device hub lumen at a position where the transition region engages the medical device hub;

the securable connector is coupled to an outer surface of the delivery conduit and is slidable along a portion thereof;

the securable connector is configured to receive the medical device hub such that the medical device hub is positioned between the surface of the delivery conduit and the securable connector; and the securable connector is secured relative to the delivery conduit so as to fluidically couple the conduit lumen with the medical device hub lumen.

15. The connector assembly of claim 14, wherein the delivery conduit contacts a wall of the of the medical device hub at two or more discrete locations and wherein the delivery conduit is spaced away from the medical device hub between the two or more discrete locations.

16. The connector assembly of claim 14, wherein the tube extends past the distal end of the delivery conduit.

17. The connector assembly of claim 14, wherein the tube is spaced away from an internal surface of the delivery conduit.

\* \* \* \* \*